(12) United States Patent
Webb et al.

(10) Patent No.: US 10,149,699 B2
(45) Date of Patent: *Dec. 11, 2018

(54) HYBRID CANNULA AND METHODS FOR MANUFACTURING THE SAME

(71) Applicant: Hybrid Cannula LP, Allen, TX (US)

(72) Inventors: Jonathan H. Webb, Allen, TX (US); Lyle Theodore Crum, Cincinnati, OH (US); Bradley Thomas Burns, Kettering, OH (US)

(73) Assignee: Hybrid Cannula LP, Allen, TX (US)

( * ) Notice: Subject to any disclaimer, the term of this patent is extended or adjusted under 35 U.S.C. 154(b) by 207 days.

This patent is subject to a terminal disclaimer.

(21) Appl. No.: 15/062,971

(22) Filed: Mar. 7, 2016

(65) Prior Publication Data

US 2016/0183970 A1    Jun. 30, 2016

Related U.S. Application Data

(63) Continuation of application No. 13/949,002, filed on Jul. 23, 2013, now Pat. No. 9,314,269, which is a
(Continued)

(51) Int. Cl.
*A61M 5/178* (2006.01)
*A61B 17/34* (2006.01)
(Continued)

(52) U.S. Cl.
CPC ...... *A61B 17/3421* (2013.01); *A61B 17/3417* (2013.01); *A61B 17/3462* (2013.01);
(Continued)

(58) Field of Classification Search
CPC ....... A61B 17/3498; A61B 2017/3441; A61M 2039/0633; A61M 2039/0686;
(Continued)

(56) References Cited

U.S. PATENT DOCUMENTS

| 5,320,611 A | 6/1994 | Bonutti et al. |
| 5,573,517 A | 11/1996 | Bonutti et al. |
| (Continued) | | |

FOREIGN PATENT DOCUMENTS

| EP | 1908428 A1 | 4/2008 |
| EP | 1908428 B1 | 1/2011 |
| (Continued) | | |

OTHER PUBLICATIONS

Dry-Doc Cannula Leak Prevention System product sheet and web site product information, ConMed Linvatec, Largo, FL, Sep. 2008, CBR 3035 Rev. 1, 3 pages.
(Continued)

*Primary Examiner* — Emily Schmidt
(74) *Attorney, Agent, or Firm* — Sprinkle IP Law Group

(57) ABSTRACT

A new process of manufacturing a hybrid cannula may include creating a first part with at least two components, overmolding at least two components of a second part to a channel in each component of the first part, and fixing the components of the first part together. The second part may include various types of features such as thick/thin dams, squirt membranes, and/or duck bill dams inside the hybrid cannula. Each dam may have any number, shape, orientation, and length of slits/openings. The slits/openings may allow passage of an instrument while the dam(s) may prevent fluid from passing through the hybrid cannula. A third part may optionally be overmolded to at least a portion of the first part, at least a portion of the second part, or both. The third part may provide an extension, a flange, or a combination thereof at a distal end of the hybrid cannula.

20 Claims, 29 Drawing Sheets

Related U.S. Application Data continuation-in-part of application No. 13/749,496, filed on Jan. 24, 2013, now Pat. No. 9,149,294.

(51) Int. Cl.
   A61M 39/02    (2006.01)
   A61M 39/06    (2006.01)
   A61B 17/00    (2006.01)

(52) U.S. Cl.
   CPC ............ *A61M 39/0247* (2013.01); *A61B 2017/00526* (2013.01); *A61B 2017/00964* (2013.01); *A61B 2017/349* (2013.01); *A61B 2017/3441* (2013.01); *A61M 2039/027* (2013.01); *A61M 2039/0261* (2013.01); *A61M 2039/0279* (2013.01); *A61M 2039/0686* (2013.01); *A61M 2207/00* (2013.01); *Y10T 29/49826* (2015.01); *Y10T 29/49908* (2015.01)

(58) Field of Classification Search
   CPC .......... A61M 39/06; A61M 2039/0646; A61M 2039/064; A61M 2039/066
   See application file for complete search history.

(56) References Cited

U.S. PATENT DOCUMENTS

| | | |
|---|---|---|
| 5,601,590 A | 2/1997 | Bonutti et al. |
| 5,667,500 A | 9/1997 | Palmer et al. |
| 5,674,240 A | 10/1997 | Bonutti et al. |
| 5,779,697 A | 7/1998 | Glowa et al. |
| 5,800,409 A | 9/1998 | Bruce |
| 5,824,002 A | 10/1998 | Gentelia et al. |
| 5,882,344 A | 3/1999 | Stouder, Jr. |
| 5,961,499 A | 10/1999 | Bonutti et al. |
| 6,338,730 B1 | 1/2002 | Bonutti et al. |
| 6,451,041 B1 | 9/2002 | Moenning et al. |
| 6,613,038 B2 | 9/2003 | Bonutti et al. |
| 6,808,492 B2 | 10/2004 | Snyder |
| 6,814,715 B2 | 11/2004 | Bonutti et al. |
| 7,413,542 B2 | 8/2008 | Kucklick et al. |
| 7,435,214 B2 | 10/2008 | Kucklick et al. |
| 7,445,596 B2 | 11/2008 | Kucklick et al. |
| 7,473,243 B2 | 1/2009 | Dennis et al. |
| 7,503,893 B2 | 3/2009 | Kucklick |
| 7,520,489 B2 | 4/2009 | Ruschke et al. |
| 7,575,565 B2 | 8/2009 | Kucklick |
| 7,896,897 B2 | 3/2011 | Gresham et al. |
| 7,993,299 B2 | 8/2011 | Kucklick |
| 7,998,061 B2 | 8/2011 | Kucklick |
| 8,012,083 B2 | 9/2011 | Kucklick |
| 8,025,648 B2 | 9/2011 | Kucklick |
| 8,038,652 B2 | 10/2011 | Morrison et al. |
| 8,092,431 B2 | 1/2012 | Lunn et al. |
| 8,118,731 B2 | 2/2012 | Kucklick |
| 8,123,676 B2 | 2/2012 | Kucklick |
| 8,430,851 B2 | 4/2013 | McGinley et al. |
| 9,119,663 B2 | 9/2015 | Webb |
| 9,149,294 B2 | 10/2015 | Webb |
| 9,314,269 B2 | 4/2016 | Webb |
| 9,398,924 B2 | 7/2016 | Webb |
| 2001/0049499 A1 | 12/2001 | Liu et al. |
| 2005/0059934 A1 | 3/2005 | Wenchell et al. |
| 2007/0088277 A1 | 4/2007 | McGinley et al. |
| 2007/0106319 A1 | 5/2007 | Au et al. |
| 2007/0255218 A1 | 11/2007 | Franer |
| 2008/0119821 A1 | 5/2008 | Agnihotri et al. |
| 2008/0294123 A1 | 11/2008 | Lunn et al. |
| 2009/0030375 A1 | 1/2009 | Franer et al. |
| 2009/0221968 A1 | 9/2009 | Morrison et al. |
| 2010/0094227 A1 | 4/2010 | Albrecht et al. |
| 2010/0185058 A1 | 7/2010 | Mastri et al. |
| 2010/0268241 A1 | 10/2010 | Flom et al. |
| 2011/0144440 A1 | 6/2011 | Crooper et al. |
| 2011/0152775 A1 | 6/2011 | Lopez et al. |
| 2012/0089160 A1 | 4/2012 | Lunn et al. |
| 2012/0089161 A1 | 4/2012 | Lunn et al. |
| 2012/0130191 A1 | 5/2012 | Pribanic |
| 2012/0165611 A1 | 6/2012 | Warren et al. |
| 2012/0245426 A1 | 9/2012 | Salvas et al. |
| 2012/0277541 A1 | 11/2012 | Bhargava et al. |
| 2012/0323081 A1 | 12/2012 | Son |
| 2013/0190573 A1 | 7/2013 | Smith |
| 2013/0303858 A1 | 11/2013 | Whittaker et al. |
| 2013/0317472 A1 | 11/2013 | Finke |
| 2014/0206942 A1 | 7/2014 | Webb |
| 2014/0207084 A1 | 7/2014 | Webb |
| 2014/0207100 A1 | 7/2014 | Webb |
| 2015/0335352 A1 | 11/2015 | Webb |

FOREIGN PATENT DOCUMENTS

| | | |
|---|---|---|
| KR | 101090665 B1 | 12/2011 |
| WO | WO2012/044959 | 4/2012 |

OTHER PUBLICATIONS

AquaLoc Cannula System product brochure, Biomet Sports Medicine, Warsaw IN, 2008, 3 pages. BSM0141.0, REV022908.

Managing fluid and sutures without compromise, Clear-Trac Complete Cannula System product brochure, Smith & Nephew, Inc., Andover, MA, Oct. 2007, 5 pages, 1061531 Rev. C.

Portion of Arthrex product brochure entitled "The Next Generation in Shoulder Repair Technology," Arthrex Inc., 2008, 7 pages.

Cannuflow, Arthroscopy without limits, Products Overview, Cannuflow, 2012, 3 pages, at <<http://www.cannuflow.com/products.html>>.

Caps-Lock cannula product brochure, ArthroCare Sports Medicine, Sunnyvale, CA, 2007, 4 pages, PN At 50-2009 Rev C.

Dri-Lok Disposable Cannula product sheet, Stryker Corp., Kalamazoo, MI, 1 pg.

Clear Cannula System product information, The new fluid management solution for all your arthroscopic procedures, DePuy Mitek, Inc., Raynham, MA, 2008, 2 pages.

Sportport™ Cannuflow product brochure, "The Easy to Use Super-Flexible Portal Cannula System that Surgeons Have Been Waiting for," Cannuflow Incorporated, 2013, 2 pages.

WECK Vista Teleflex™ brochure, 2012, 6 pages.

International Search Report and Written Opinion issued for PCT Application No. PCT/US2013/068977, dated Jan. 30, 2014, 10 pages.

International Search Report and Written Opinion issued for PCT Application No. PCT/US2013/068978, dated Jan. 30, 2014, 8 pages.

International Search Report and Written Opinion issued for PCT Application No. PCT/US2013/068975, dated Feb. 20, 2014, 8 pages.

Office Action issued for U.S. Appl. No. 13/749,492, dated Dec. 24, 2014, 8 pages.

Office Action issued for U.S. Appl. No. 13/749,496 , dated Jan. 7, 2015, 8 pages.

Notice of Allowance issued for U.S. Appl. No. 13/749,492, dated Apr. 24, 2015, 7 pages.

Office Action issued for U.S. Appl. No. 13/749,496, dated May 13, 2015, 11 pages.

Notice of Allowance issued for U.S. Appl. No. 13/749,492, dated Jul. 21, 2015, 7 pages.

Notice of Allowance issued for U.S. Appl. No. 13/749,496, dated Aug. 5, 2015, 7 pages.

International Preliminary Report on Patentability (IPRP) issued for PCT Application No. PCT/US2013/068975, dated Aug. 6, 2015, 7 pages.

International Preliminary Report on Patentability (IPRP) issued for PCT Application No. PCT/US2013/068977, dated Aug. 6, 2015, 9 pages.

Office Action for U.S. Appl. No. 13/949,002, dated Sep. 1, 2015, 9 pages.

Notice of Allowance issued for U.S. Appl. No. 13/949,002, dated Dec. 10, 2015, 8 pages.

(56) References Cited

OTHER PUBLICATIONS

International Preliminary Report on Patentability issued for PCT Application No. PCT/US2013/068978, dated Feb. 4, 2016, 7 pages.
Notice of Allowance issued for U.S. Appl. No. 14/814,105, dated Mar. 2, 2016, 7 pages.

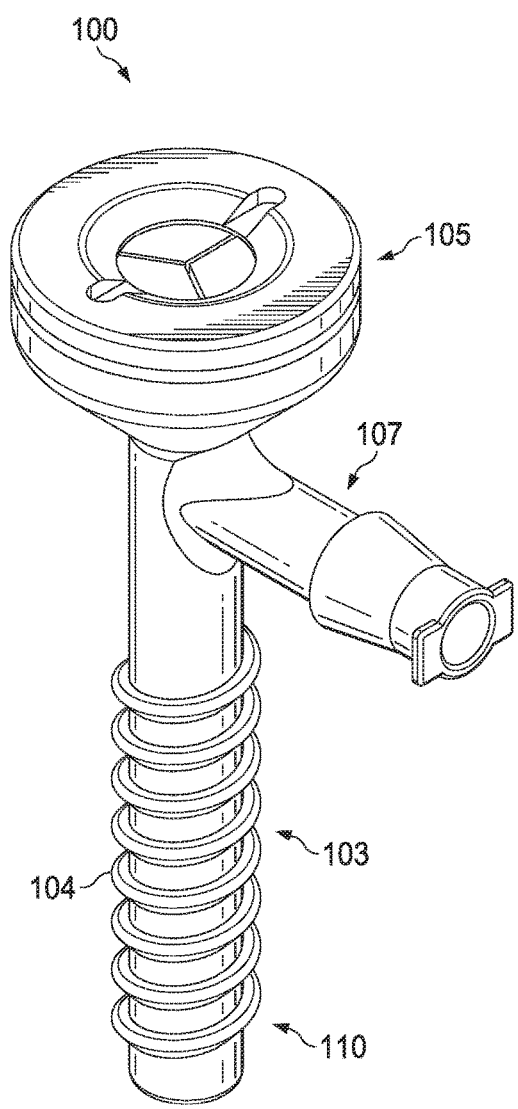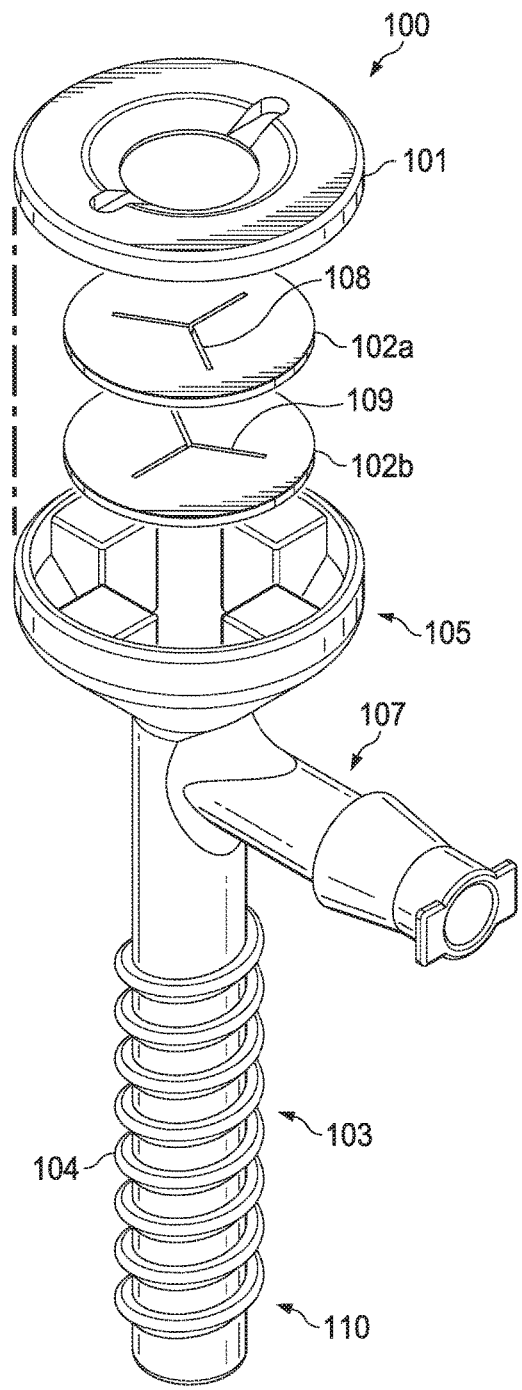
FIG. 1a
(PRIOR ART)
FIG. 1b
(PRIOR ART)

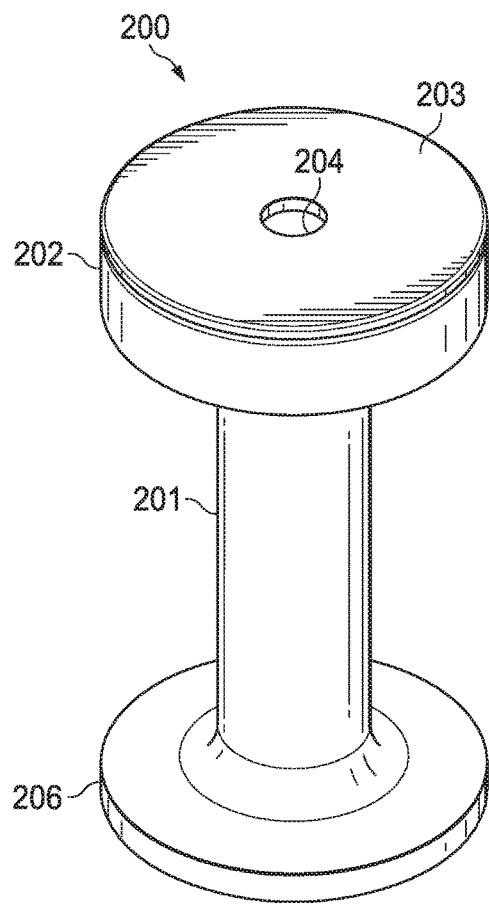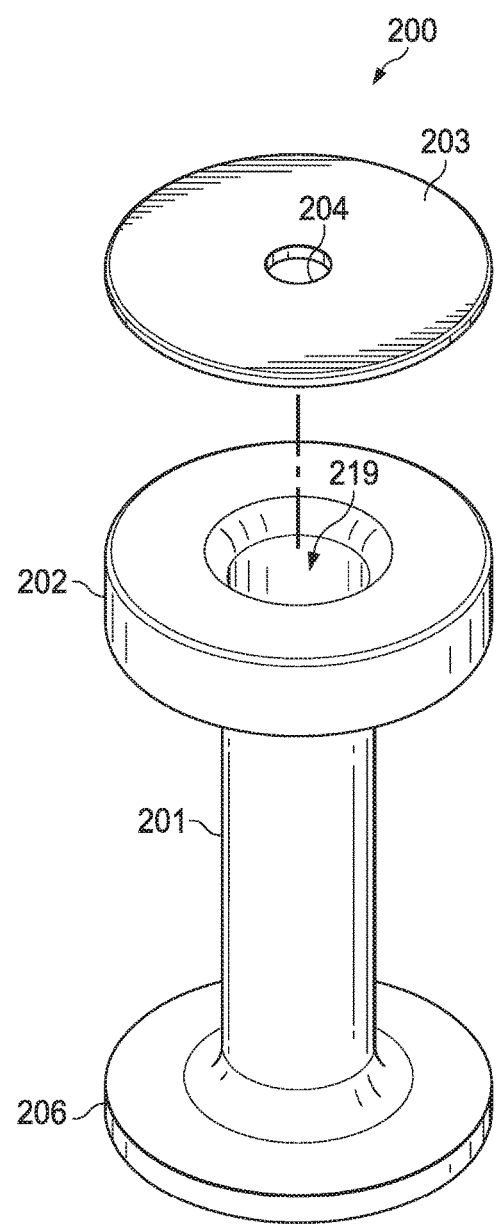
FIG. 3a
(PRIOR ART)
FIG. 3b
(PRIOR ART)

HYBRID CANNULA AND METHODS FOR MANUFACTURING THE SAME

CROSS-REFERENCE TO RELATED APPLICATIONS

This is a continuation of, and claims a benefit of priority from U.S. patent application Ser. No. 13/949,002, filed Jul. 23, 2013, which is a continuation-in-part application of U.S. patent application Ser. No. 13/749,496, filed Jan. 24, 2013, now U.S. Pat. No. 9,149,294, entitled "HYBRID CANNULA AND METHODS FOR MANUFACTURING THE SAME," which relates to U.S. patent application Ser. No. 13/749,492, filed Jan. 24, 2013, now U.S. Pat. No. 9,119,663, entitled "HYBRID CANNULA AND METHODS FOR MANUFACTURING THE SAME." All patent applications listed in this paragraph are hereby incorporated by reference in their entireties.

TECHNICAL FIELD

This disclosure relates generally to surgical portal devices and, more particularly, to a hybrid cannula having a multi-piece rigid part overmolded with a multi-piece non-rigid part, forming multiple dams therein, the hybrid cannula being useful in minimally invasive surgical procedures, including arthroscopic and endoscopic surgeries.

BACKGROUND

It is often preferable to perform a surgery as a minimally invasive surgery (endoscopy or arthroscopy) rather than as an open surgery. Endoscopy and arthroscopy are performed through the use of portals. These portals, made through incisions in the skin and some portion of underlying tissue, are used to fill the abdomen with air, in the case of endoscopy, and the surgical space with fluid, in the case of arthroscopy.

For the duration of this disclosure minimally invasive surgery will be described as it pertains to arthroscopic surgery; however, it is seen that the disclosure extends into endoscopy as well as arthroscopy and the invention disclosed should not be limited to arthroscopy.

A cannula is a medical device having an internal passage (or "cannulation"). A cannula can be inserted into a body, often to create a pathway for elongated instruments to pass into and out of the surgical space. During arthroscopy, as mentioned before, fluid is inserted into the surgical space (such as the shoulder) in order to pressurize and distend the surgical space and improve visualization through the arthroscope. One reason a cannula is inserted into the portal is to prevent this fluid from escaping out of the body.

The cannula functions to prevent fluid from escaping from the surgical space while instruments are inserted through the passage in the cannula as well as when no instruments are located in the cannula. This is typically performed by incorporating a flexible dam with slits into the passage in the cannula.

Cannulas generally consist of a proximal end, an elongated cannulated body, and a distal end.

FIGS. 1a-1b and 2a-2b depict views of a prior art cannula. A typical cannula 100 is made of a rigid plastic while flexible dams 102a and 102b are incorporated into the proximal end of the device and held in place by cover 101. The rigidity of the cannula's elongated body 103 allows the device to simply be threaded using thread 104 through the portals in tissue 10 and positioned over a site, such as depicted in FIG. 2a. However, because this type of cannula has a large moment arm (MA), it has a tendency to tip over when instruments are inserted through it, as depicted in FIG. 2b. For this reason, cannula 100 often has to be held in place while inserting instruments through the device, which is not desirable.

FIGS. 3a-3b and 4 depict views of another approach. Cannula 200 is made of a flexible material, with a passage 219 along elongated body 201 and a flexible dam 205 is incorporated into passage 219 along elongated body 201. Thin dam 203 may be attached at the proximal end of cannula 200.

Flexible flanges 202 and 206 are found on the proximal and distal ends of the device, and the length of cannula 200 is approximately the thickness of the skin and some portion of underlying tissue. This device has a tendency to remain in place and upright during instrument insertion. However, the device is inserted through the portal using a non-standard method, which is not desirable. An example of a non-standard method may involve holding the distal end of cannula 200 with the jaws of a grasping tool, advancing the jaws of the grasping tool and the distal end of cannula 200 together into the portal, and opening the jaws of the grasping tool to release cannula 200 from the grasping tool after the distal end of cannula 200 exits the portal and can be detected visually by surgical personnel.

SUMMARY OF THE DISCLOSURE

The disclosed methods and products detailed below serve in part to address the advantages and disadvantages of various types of cannulas described above.

In some embodiments, a cannula may be manufactured by a process comprising creating a first part and overmolding a second part to the first part. The first part may have two or more components which may be identical to one another and may be fixed together to form the first part. Each of the two or more components of the first part may have a proximal end, a distal end, and a channel extending between the proximal end and the distal end. The first part is made of a rigid material and may be made using a first mold. Examples of a suitable rigid material may include, but are not limited to, polycarbonate, polyetheretherketone (PEEK), acrylonitrile butadiene styrene (ABS), polyethylene, titanium, stainless steel, other plastics and metals, etc. The first part may provide the structure of the body of the hybrid cannula.

In some embodiments, the second part may also have two or more components. The two or more components of the second part may also be identical to one another. Each of the two or more components of the second part may be created by overmolding a non-rigid material to the channel of each of the two or more components of the first part. Examples of a suitable non-rigid material may include, but are not limited to, an elastic substance such as thermoplastic elastomer, polyurethane, silicone, rubber, etc. The second part may include various types of features including but not limited to thick dams, thin dams, duck bill dams, and/or squirt membranes inside the hybrid cannula.

The two or more components of the first part may be fixed together by gluing, bonding, welding, interlocking, mechanical fitting, etc. to create a unit, for instance, one that resembles a tube such that the two or more components of the second part form at least one dam inside the tube. In some embodiments, the process may further include creating an opening in the at least one dam or it may be left with "natural slit/s" and not require post processing to create an opening. Each dam may have any number, shape, orientation, and length of slits. The slits in the dam may allow passage of an instrument through the hybrid cannula while the dam(s) may prevent air or fluid from passing through the hybrid cannula.

In some embodiments, the cannula may include only the first part and the second part. In such embodiments, the first part may have external threads, rings, or protrusions. In some embodiments, the second part may be overmolded to a portion of the inner surface of the first part. In some embodiments, the second part may be overmolded to the entire length of the first part. In such embodiments, the second part could include internal features such as dam(s) and/or external features such as threads, rings, and/or protrusions. In some embodiments, the second part may provide an extension, a flange, or a combination thereof at a distal tip of the cannula.

In some embodiments, the process may further include creating a third part by overmolding the unit, for instance, which may resemble a tube, with a non-rigid material. In some embodiments, the second part and the third part may be made of the same non-rigid material. The third part may provide an extension, a flange, or a combination thereof at a distal end of the hybrid cannula. The third part may have a smooth surface or it may have external threads, rings, and/or protrusions. Again, in some embodiments, the third part is not required for the hybrid cannula to function.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

It is to be noted, however, that the appended drawings illustrate only exemplary embodiments of the invention and are therefore not to be considered limiting of its scope for the invention which may admit to other equally effective embodiments. In addition, although the figures may depict embodiments wherein the components represent different devices or locations, they can be combined into a single device or location. Also, a single component may be comprised of a combination of components.

FIG. 1a depicts a rigid cannula.

FIG. 1b depicts the cannula of FIG. 1a in an exploded view.

FIG. 3a depicts a flexible cannula.

FIG. 3b depicts the cannula of FIG. 3a in an exploded view.

FIG. 4 depicts a cross-sectional view of the cannula of FIG. 3a.

DETAILED DESCRIPTION

Figure 2A:
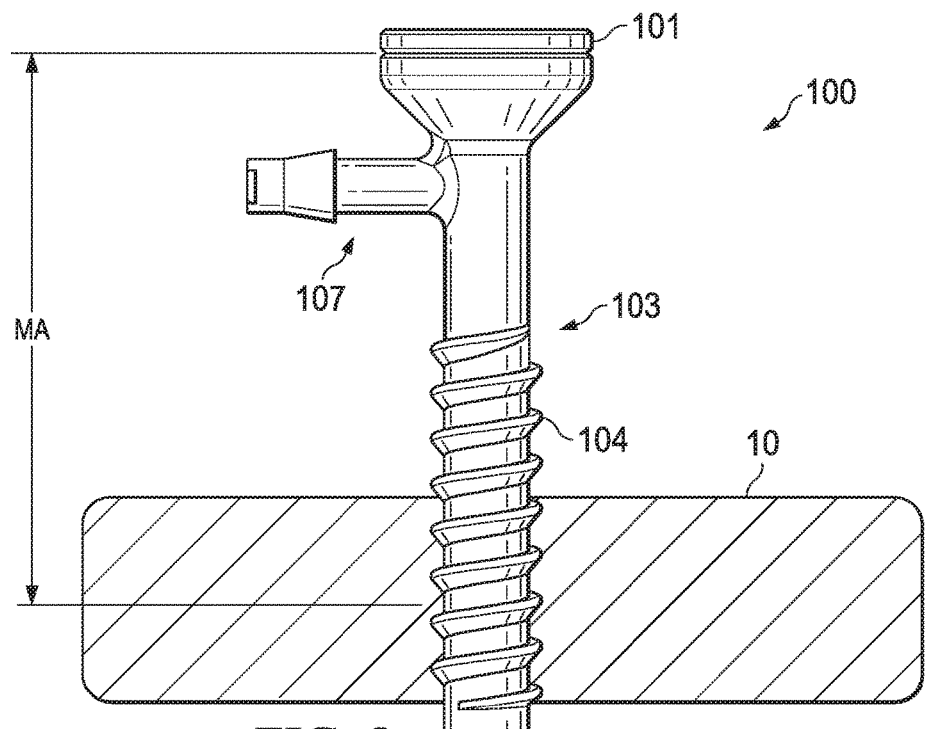
FIG. 2a depicts the cannula of FIG. 1a inserted through the soft tissue.
Figure 2B:
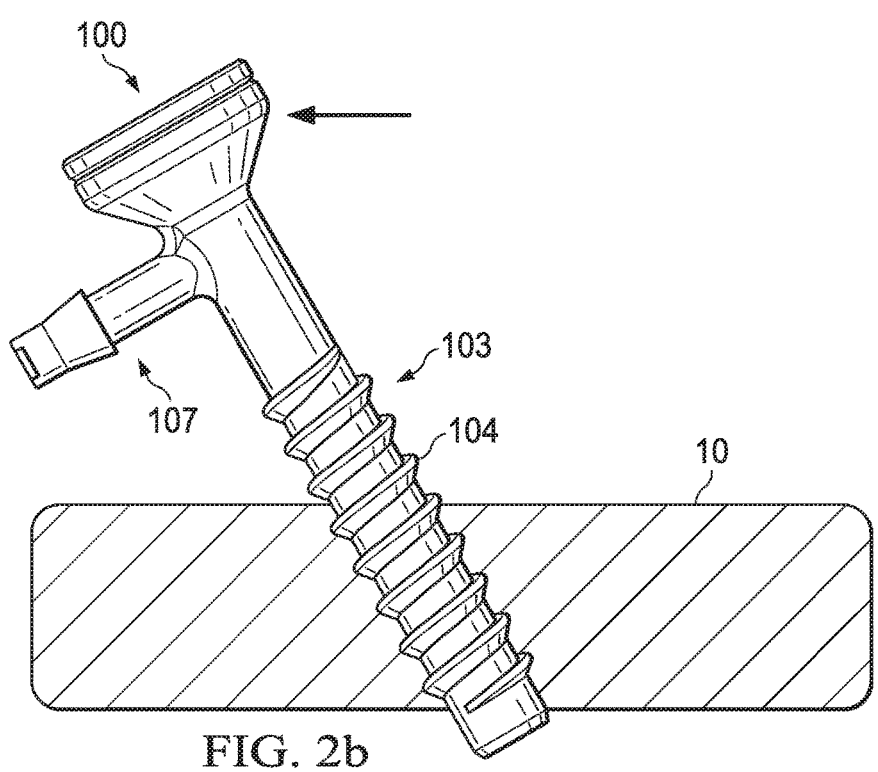
FIG. 2b depicts the cannula of FIG. 1a inserted through the soft tissue, while the moment placed on it by the force of inserting an instrument through the cannula has caused it to begin to tilt.

Embodiments of hybrid cannulas disclosed herein can overcome the shortcomings of conventional cannulas. Using manufacturing methods not traditionally utilized for cannulas, a new device may be created to have the ability, among others, to remain stable during instrument insertion and to be inserted through the portal using traditional methods. Those skilled in the art will recognize that the invention can be used in both arthroscopic and endoscopic surgery without departing from the spirit or scope of the invention.

Referring first to FIG. 1a, a typical arthroscopic cannula 100, which is fully assembled, is depicted. Most generally, arthroscopic cannula 100 consists of distal end 110, cover 101, and proximal end 105 where functioning dams 102a and 102b are attached to the device, as shown in FIG. 1b. FIG. 1b depicts an exploded view of cannula 100.

The following steps outline a general method for manufacturing cannula 100, although variations to this method may exist.

The cannula's elongated body 103 and cover 101 may be manufactured separately from a similar rigid material using, for instance, separate single-shot molding processes. Elongated body 103 may be formed with stop cock 107 to accommodate attachments such as inflow or outflow pump tubing. Dams 102a and 102b may be manufactured from a flexible material and function to prohibit fluid from passing through cannula 100. Flexible dams 102a and 102b may be made in various ways. For example, dams 102a and 102b can be manufactured via molding and/or die cutting processes. In a molding process, dams 102a and 102b are first molded. Slits 108 and 109 are then created in dams 102a and 102b. In a die cutting process, a flat sheet of flexible material such as rubber is cut into a circular shape using a die. The die may also cut slits 108 and 109 into dams 102a and 102b, or a secondary slitting operation could be used to create slits 108 and 109 in dams 102a and 102b. Die cutting the flexible material may be the preferred method to manufacture dams 102a and 102b because it is a relatively inexpensive process as compared to molding.

Traditionally, cannula 100 components are assembled and fixed together using methods such as adhesion and/or mechanical fixation. It is important to note that elongated body 103, dams 102a and 102b, and cover 101 must be assembled together in a secondary operation. Specifically, the axis of dam 102a is rotationally offset from the axis of dam 102b so that the dams' slits 108 and 109 are not aligned. Dams 102a and 102b are placed between elongated body 103 and cover 101. Elongated body 103 and cover 101 are rigidly fixed to one another using any number of fixations including but not limited to adhesives or mechanical fixation.

Figure 4:
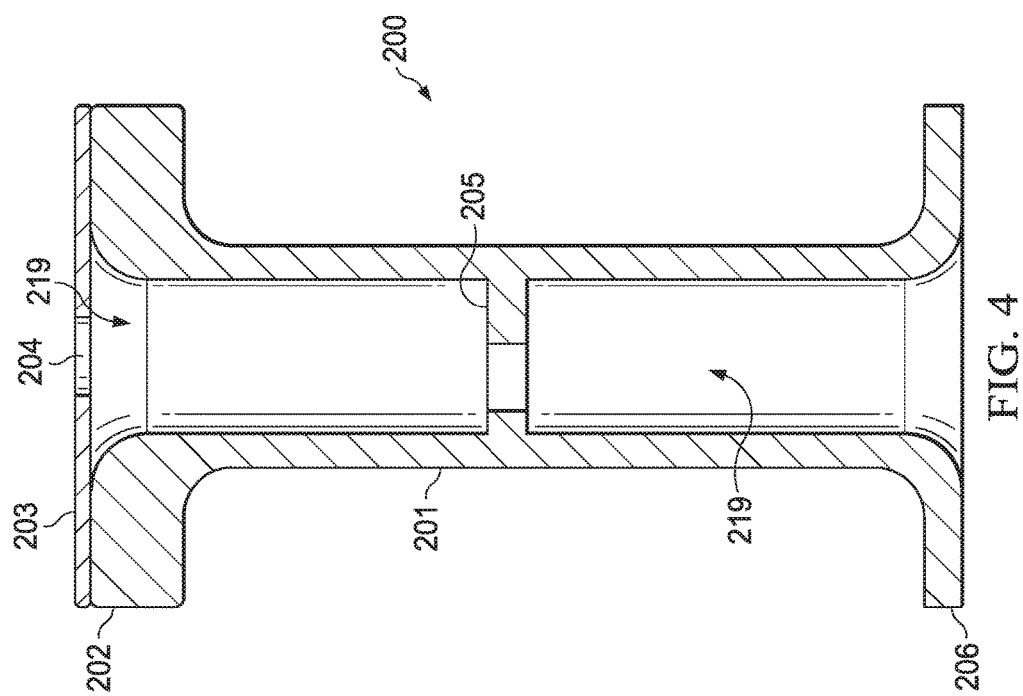

Referring next to FIG. 3a, another arthroscopic cannula 200 may be flexible and have flanges on both ends. In FIG. 3b, an exploded view of cannula 200 exposes components of which cannula 200 comprises. Elongated body 201 with flanges 202 and 206, and thin dam 203 are typically made from the same material, which may be a flexible rubber, silicone, or the like. FIG. 4 depicts a cross-sectional view of cannula 200, showing dam 205 positioned inside passage 219 in elongated body 201.

The following steps outline a general method for manufacturing cannula 200, although variations to this method may exist.

Cannula 200 may be manufactured by a single shot molding process. The mold from the single shot molding process includes features to account for flanges 202 and 206 as well as dam 205, which is integral to elongated body 201. As a result of this single shot molding process, dam 205 and elongated body 201 must be manufactured from the same flexible material, such as rubber, silicone, or the like. This allows for dam 205 to remain flexible and maintain similar properties as dams 102a and 102b in cannula 100. Additionally, using this process enables dam 205 to be integral to elongated body 201 and be located inside passage 219 of elongated body 201. After molding, a secondary slitting operation is then used to create slits in dam 205. Thin dam 203 may be manufactured from a number of processes. One process is to mold thin dam 203 with a small aperture 204 or die cut small aperture 204 after molding thin dam 203, while a second method is to die cut thin dam 203 with a small aperture 204 from a sheet of flexible material such as rubber.

Thin dam 203 may be attached to flange 202 on elongated body 201. This may be accomplished by any number of chemical, mechanical, or thermal methods, including but not limited to a mechanical fit.

Cannula 200 is characterized by several disadvantages. Some of these disadvantages include cannula 200 may be too flexible for use with traditional insertion procedures, cannula 200 may move up and down within the portal during instrument insertion and/or removal, or the like.

Common features of both cannula 100 and cannula 200 are the flexible dams. In the case of the rigid cannula 100, general practice is to assemble dams 102a and 102b to rigid parts 101 and 103 of cannula 100 using secondary operations. In the case of flexible cannula 200, elongated body 201 and flanges 202 and 206 are molded from the same material as dam 205, eliminating the need to assemble dam 205 to elongated body 201. As will be shown below, embodiments disclosed herein leverage manufacturing methods not typically used in manufacturing cannulas, in order to create a device which can provide some of the advantages of cannula 100 and cannula 200 without some of their respective drawbacks.

In one embodiment, a hybrid cannula may include a rigid portion with a flexible portion formed with a dam and/or membrane in an internal passage of the cannula. The flexible portion may be overmolded onto the rigid portion. In one embodiment, the rigid portion and the flexible portion may partially overlap as a result of an overmolding process.

Figure 5:
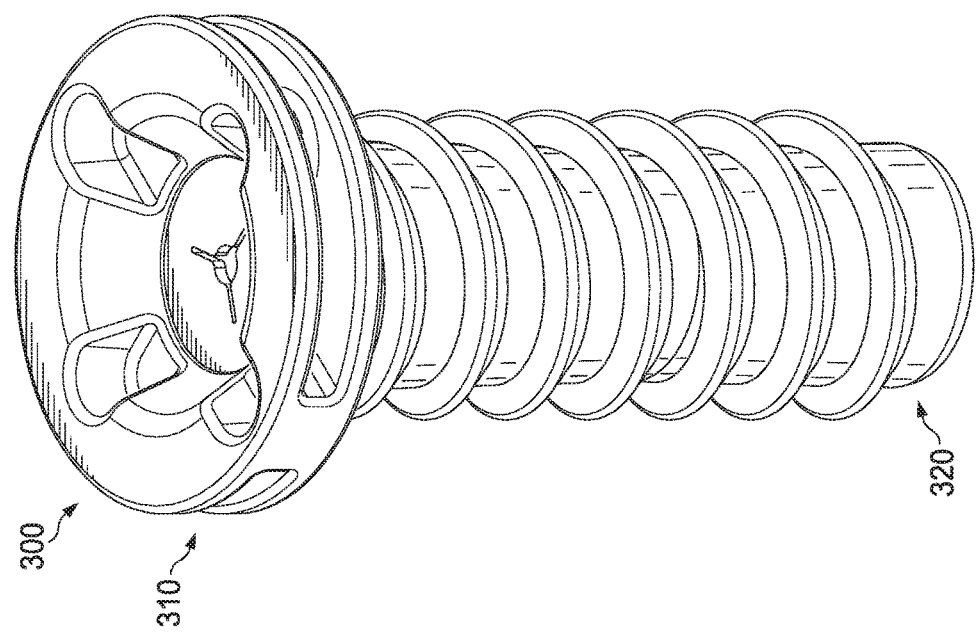
FIG. 5 depicts an isometric view of one embodiment of a hybrid cannula.
Figure 6:
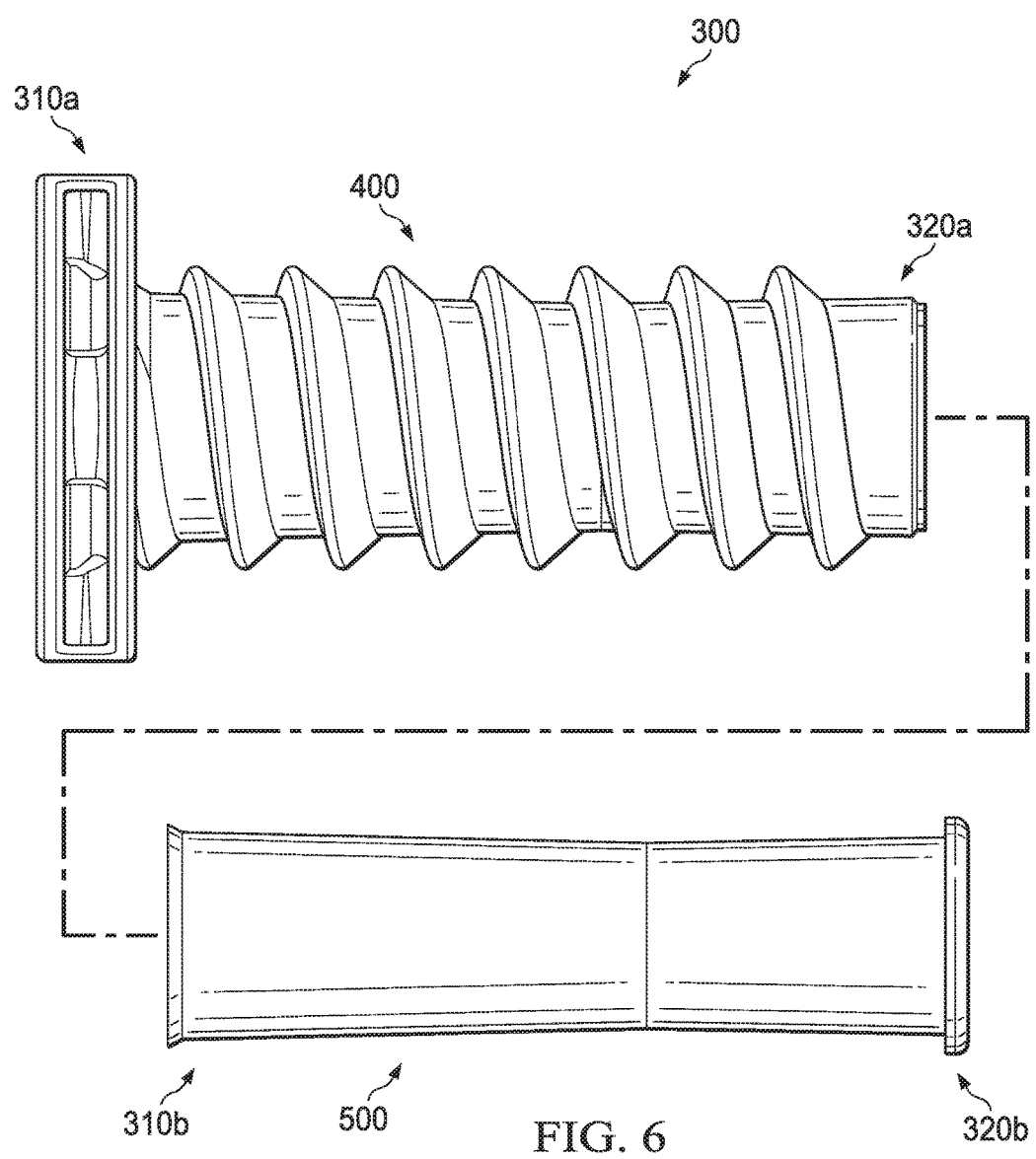
FIG. 6 depicts an exploded view depicting portions of one embodiment of a hybrid cannula.

One example of a hybrid cannula is depicted in FIG. 5. Hybrid cannula 300 may comprise proximal end 310 and distal end 320. An exploded view of hybrid cannula 300 is depicted in FIG. 6. First portion 400 of hybrid cannula 300 may be made of a material with selected rigidity so that it is rigid enough to be easily inserted or positioned in a patient using traditional insertion methods, and may be formed to have an elongated shape or profile from proximal end 310 to distal end 320 (as seen in FIG. 5). Second portion 500 of hybrid cannula 300 may be flexible and contain one or more features to prevent fluid leakage and/or squirting.

Figure 7A:
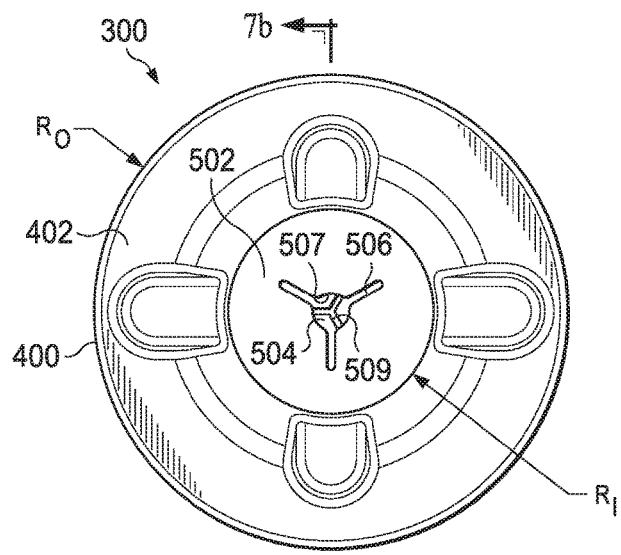
FIGS. 7a and 7b depict a top view and a cross-sectional view of one embodiment of a hybrid cannula.
Figure 7B:
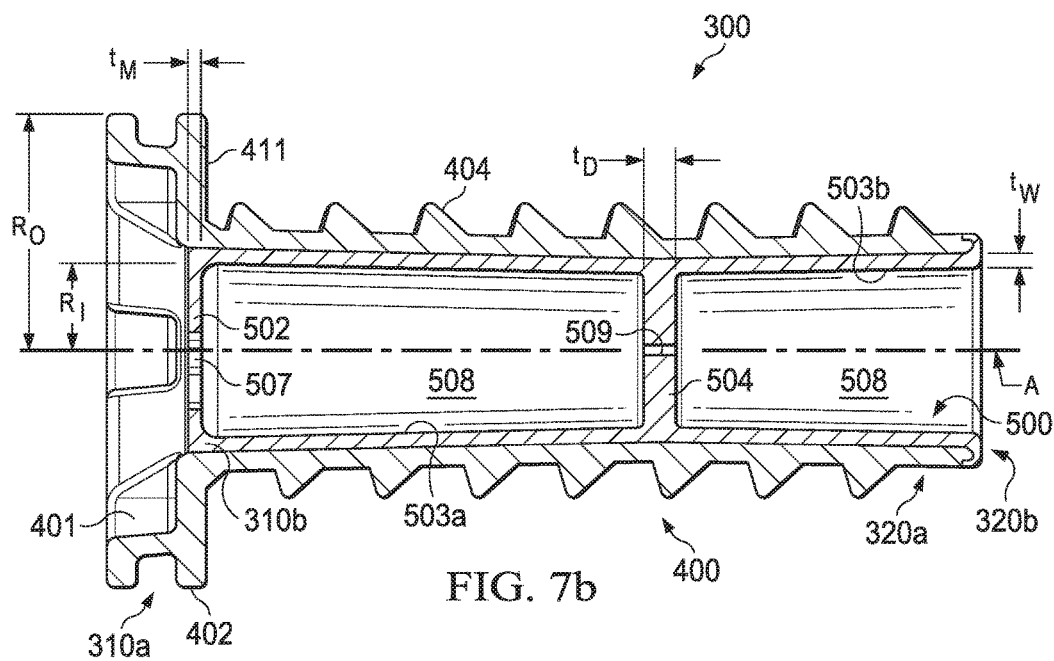

FIGS. 7a and 7b depict a top view and a cross-sectional view of hybrid cannula 300 in which second portion 500 may be formed partially inside first portion 400. This may be established in any number of ways including but not limited to overmolding second portion 500 to first portion 400. As depicted in FIGS. 7a and 7b, hybrid cannula 300 having passage 508 formed therein may include first portion 400 which may include an outer surface formed with thread 404 and flange 402 having outer radius $R_O$ and having inner radius $R_I$. The ratio of $R_O/R_I$ may be selected to minimize the overall size of hybrid cannula 300 while still maintaining its structural integrity. In some embodiments, the ratio may be selected to minimize the overall size of flange 402.

Second portion 500 may be formed from various materials. Second portion 500 may be formed in first portion 400 and include dam 504 having slit(s) 509, thin membrane 502, and walls 503a and 503b. Dam 504 may have a thickness $t_D$, thin membrane 502 may have a thickness $t_M$, and walls 503a and 503b may have a thickness $t_W$. Thin membrane 502 may be formed with slots 506 and positioned at proximal end 310b. Opening 507 may also be formed in membrane 502. Opening 507 and slots 506 may be configured to allow for a core pin or tool necessary for molding to maintain structural integrity during the manufacturing process. As depicted in FIG. 7a, dam 504 may be visible through opening 507, including slits 509. Opening 507 and slot(s) 506 and slits 509 may be aligned about a central or longitudinal axis A, and dam 504 and thin membrane 502 may be oriented relative to each other such that slots 506 and slits 509 do not align. Distal end 320b of second portion 500 may or may not extend over distal end 320a of first portion 400. Additionally, proximal end 310b of second portion 500 may or may not extend past proximal end 310a of first portion 400.

Hybrid cannula 300 may be manufactured to a number of different overall lengths. A correctly sized length of hybrid cannula would be selected for use during the arthroscopy based on the thickness of the soft tissues that the portal extends through.

Figure 8A:
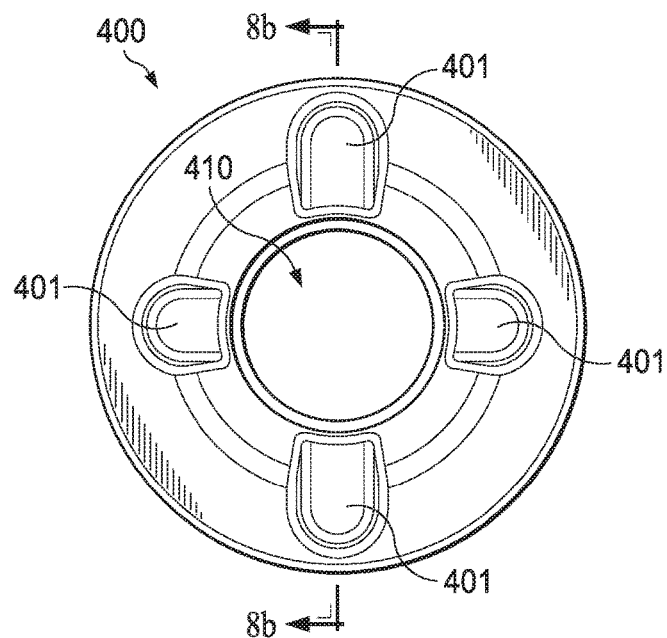
FIGS. 8a and 8b depict a top view and a cross-sectional view of a portion of one embodiment of a hybrid cannula.
Figure 8B:
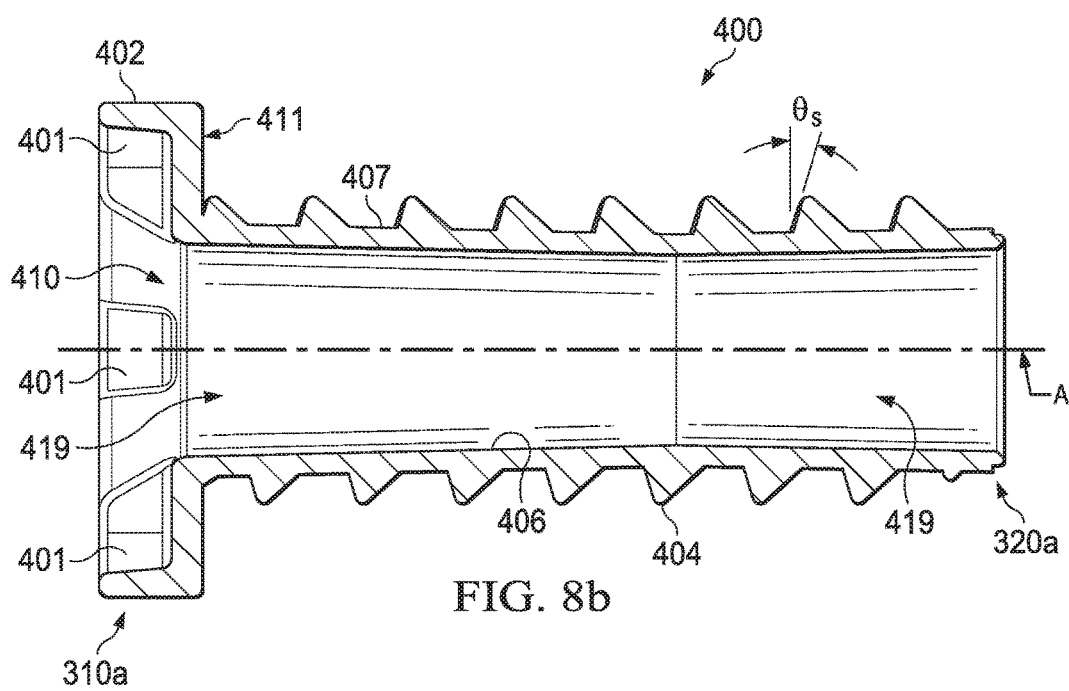

FIGS. 8a and 8b depict a top view and a cross-sectional view of first portion 400 of hybrid cannula 300. Embodiments of first portion 400 may extend between proximal end 310a and distal end 320a of hybrid cannula 300. Additionally, there may be flange 402 at proximal end 310a and thread(s) 404 along the outside of first portion 400.

First portion 400 of hybrid cannula 300 may be composed of one material or several materials. Additionally, each feature of first portion 400 may be made of only one material or of several materials. The materials of each feature may be flexible, rigid, or semi-rigid. Examples of rigid materials that may be used in first portion 400 and may be appropriate for use in surgery may include, but are not limited to, polycarbonate, polyetheretherketone (PEEK), and acrylonitrile butadiene styrene (ABS). Examples of flexible materials that may be used in first portion 400 may be appropriate for use in surgery and may include, but are not limited to, silicone, thermoplastic elastomer, polyurethane, and rubber. Other materials may be used for overmolding onto, for example titanium and stainless steel. For both flexible and rigid materials, it may be beneficial for the material to include colorants and/or to be partially transparent. Plastic or stainless steel are generally accepted by the orthopedic community. Some embodiments of hybrid cannula 300 disclosed herein can be lighter in weight than a conventional cannula, such as cannula 100. The reduction in weight of hybrid cannula 300 relative to cannula 100 may be caused by the elimination and/or size reduction of one or more features of cannula 100. For example, hybrid cannula 300 may not include a stop cock such as stop cock 107 of cannula 100. As another example, selected for the same patient, hybrid cannula 300 may be shorter in length relative to cannula 100.

Figure 16A:
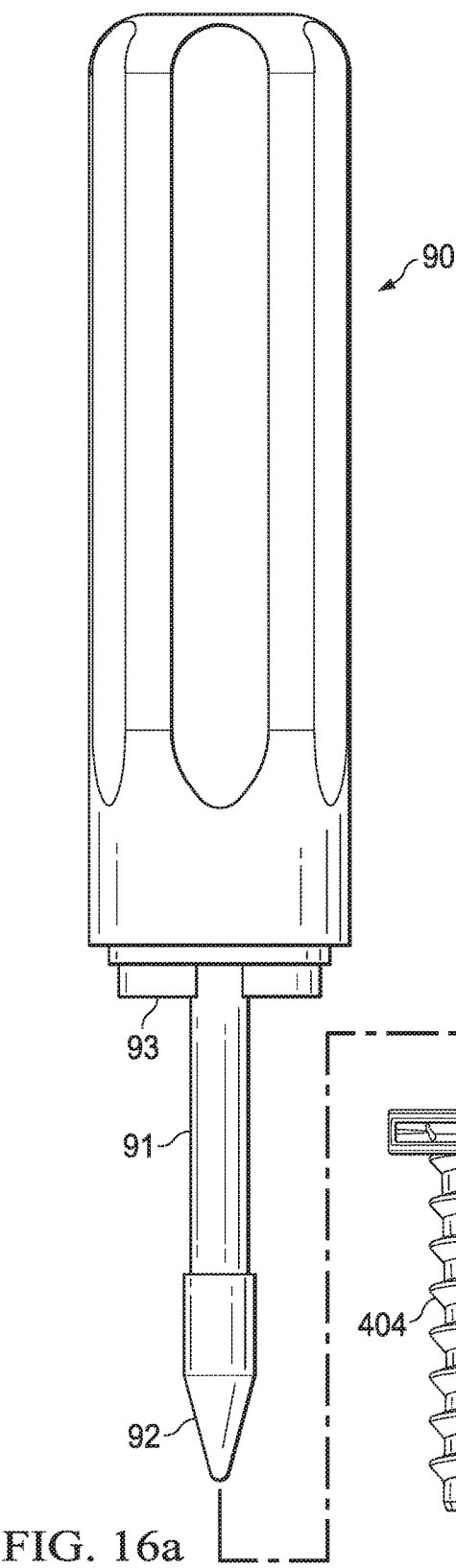
FIG. 16a depicts a side view of one embodiment of a hybrid cannula and a tool useful for inserting a cannula.
Figure 16B:
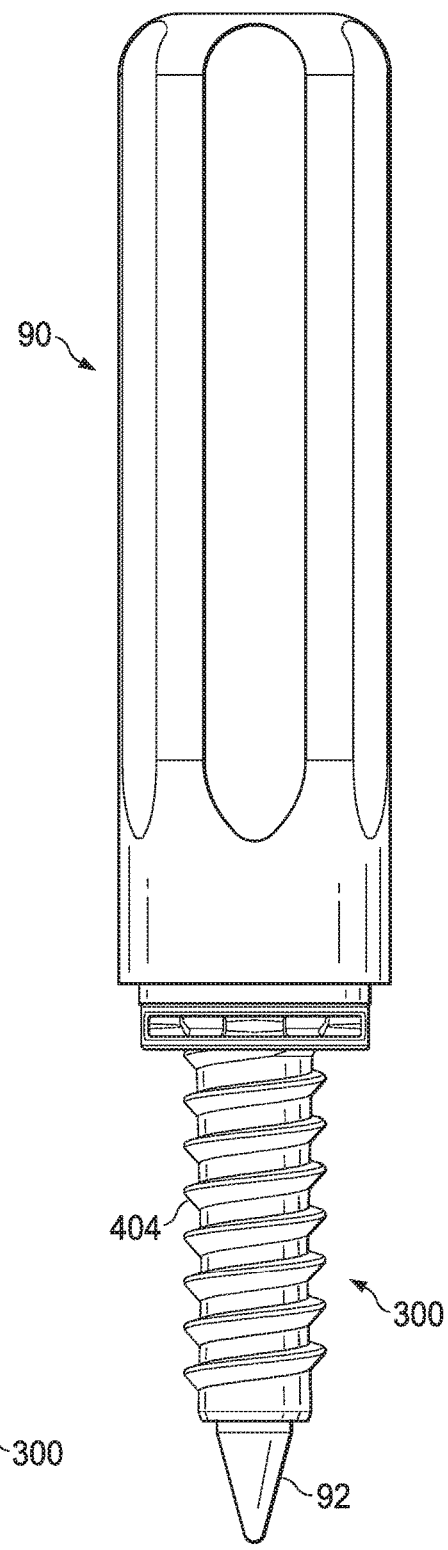
FIG. 16b depicts a side view of one embodiment of a hybrid cannula coupled with a tool useful for inserting a cannula.

Proximal end 310 of hybrid cannula 300 may include flange 402. Hybrid cannula 300 can be inserted in a manner similar to cannula 100 described above, and various features of hybrid cannula 300 can provide several additional advantages. For example, flange 402 at proximal end 310 of hybrid cannula 300 may prevent hybrid cannula 300 from being over inserted by providing a surface 411 to press against the skin, stopping hybrid cannula 300 from being inserted further than the base of flange 402. Additionally, flange 402 provides a surface for features 401 which allow an insertion instrument (an example is depicted in FIGS. 16a and 16b, discussed below) to contact hybrid cannula 300 and insert it through the portal. Features 401 may be any size or shape which allows for an opposing shape or complimentary feature on an insertion instrument to insert and provide a resistance to the torque and/or force placed on hybrid cannula 300 during insertion of hybrid cannula 300 through the portal. Additional advantages will be apparent to those skilled in the art.

First portion 400 may be cannulated or otherwise include passage 419 with opening 410 to allow instruments to pass through during arthroscopy. Inner surface 406 may also be appropriately shaped for material to adhere to it. Additionally, first portion 400 may or may not be uniformly thick and could have a number of features built into inner surface 406 or outer surface 407, including but not limited to ribbing, holes, steps, threads, and slots.

External threads 404 may function to aid in insertion threading of hybrid cannula 300 into the soft tissue surrounding the portal. Additionally, external threads 404 may function to hold hybrid cannula 300 in place in the soft tissue throughout the surgery, including during instrument insertion and removal. External threads 404 may start at or near flange 402 and may lead out of the hybrid cannula at or near distal end 320a of first portion 400. External threads 404 may start any distance past flange 402 and end any distance before distal end 320a. For example, one skilled in the art would appreciate that in some applications it would be beneficial for only the portion near distal end 320a to contain external threads. External threads 404 shown may have a constant pitch and profile; however, a variable pitch and/or a variable profile of external threads 404 could be used to aid in engaging the soft tissue. Additionally, angle $\Theta_S$ of profile of external threads 404 may be generally perpendicular to or angled relative to longitudinal axis A. Additionally, the profile of thread 404 may be any shape including but not limited to trapezoidal, circular, rectangular, triangular, ovular, and asymmetric shapes.

Figure 9A:
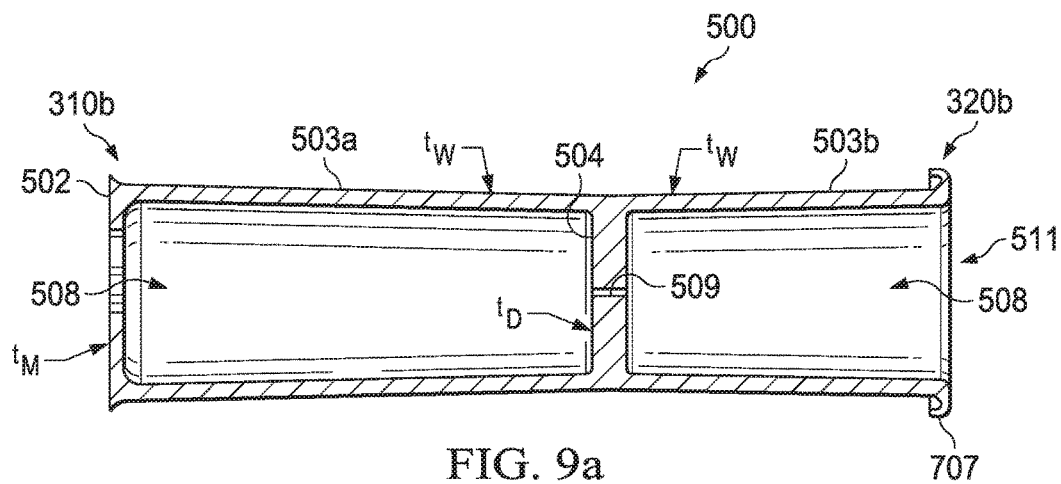
FIGS. 9a and 9b depict a cross-sectional view and a top view of another portion of one embodiment of a hybrid cannula.
Figure 9B:
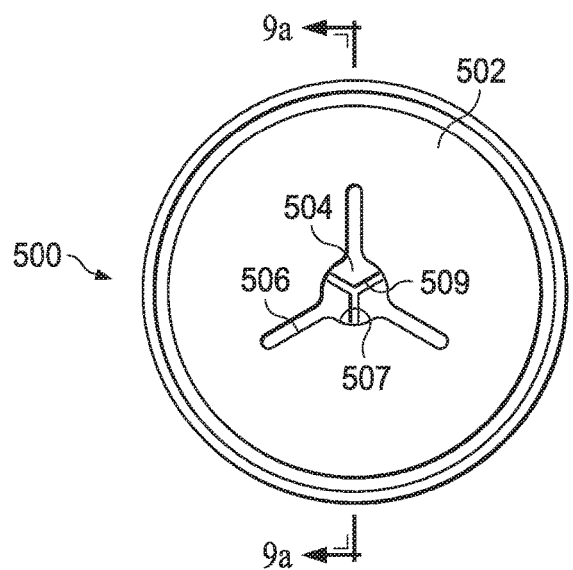

FIGS. 9a and 9b depict a cross-sectional view and a top view of second portion 500 of hybrid cannula 300. Second portion 500 may comprise proximal end 310b, body regions or bodies 503a-503b, and distal end 320b. Second portion 500 may include passage 508 from thin membrane 502 at proximal end 310b along the length of hybrid cannula 300 to opening 511 at distal end 320b. The inner diameter of passage 508 may be constant along the length of second portion 500 or may vary. In some embodiments, the inner diameter of passage 508 may vary due to thickness $t_W$ of walls 503a or 503b. In some embodiments, the inner diameter of passage 508 may vary due to the inner diameter of first portion 400.

At proximal end 310b of second portion 500, membrane 502 (also referred to as a squirt membrane) may be found. Thickness $t_M$ of membrane 502 can be of any suitable thickness, depending upon the elasticity, durometer, and/or strength of the material used. Examples of a suitable thickness may range from about 0.25 mm to about 2 mm. Thickness $t_M$ of the membrane can be about the same as or less than thickness $t_D$ of dam 504.

A purpose of squirt membrane 502 may include preventing fluid from being expelled from ("squirting out of") hybrid cannula 300 during instrument insertion or removal. For example, when an arthroscopic instrument is passed through or removed from hybrid cannula 300 the pressure behind dam 504 may cause fluid to squirt through dam 504 and around the instrument. Squirt membrane 502 may provide a secondary surface to prevent the fluid from exiting proximal end 310b of hybrid cannula 300 and striking the surgeon. The thickness $t_M$ of squirt membrane 502 may be small to prevent significant resistance to the arthroscopic instrument when the instrument is inserted through the device. Squirt membrane 502 may be flexible so that the movement of the instrument within hybrid cannula 300 is not restricted.

As illustrated in FIG. 9a, dam 504 may be positioned in passage 508 between proximal end 310b and distal end 320b of second portion 500. The thickness of the dam can be about the same as or more than the thickness of squirt membrane 502 described above. At distal end 320b of second portion 500 of hybrid cannula 300, a feature which may allow second portion 500 to be molded throughout the entire length of first portion 400 may be found. For example, protrusion 707 at distal end 320b may be a feature that can be used as a seal-off during overmolding of second portion 500 onto first portion 400. It can be appreciated that a number of different types of seal-offs may be used distal or proximal to dam 504 in order to overmold second portion 500 onto first portion 400. A seal off may be on squirt membrane 502 during overmolding as well. In embodiments in which the squirt membrane is not present, seal-offs may be on walls 503a and 503b, both distal and proximal to dam 504.

Second portion 500 of hybrid cannula 300 may be composed of one material or several materials. The materials of each feature may be flexible, semi-rigid, or rigid. Examples of these flexible and semi-rigid materials that may be used to manufacture second portion 500 and may be appropriate for use in surgery include, but are not limited to, silicone, thermoplastic elastomer, polyurethane, and rubber. Examples of rigid materials that may be used in second portion 500 and may be appropriate for use in surgery may include, but are not limited to polycarbonate, polyetheretherketone (PEEK), and acrylonitrile butadiene styrene (ABS). Other materials may be overmolded onto, for example titanium and stainless steel. It may also be beneficial for the materials to include colorants and/or to be partially transparent.

In second portion 500, squirt membrane 502 and dam 504 may be connected by body region 503a. However, it may be found in some embodiments of second portion 500 body regions 503a-503b may not connect one feature to another. For example, in one embodiment possibility, protrusion 707 may be connected to dam 504 by body region 503b, but squirt membrane 502 might not be connected to dam 504 by body region 503a. Therefore, dam 504 and squirt membrane 502 may be formed during two separate processes.

As mentioned above, proximal end 310b may include squirt membrane 502. An advantage of squirt membrane 502 is that it may prevent fluid from squirting out of hybrid cannula 300 during instrument insertion or removal. When an arthroscopic instrument is passed through hybrid cannula 300, fluid pressure behind dam 504 may cause fluid to squirt through dam 504 and around the instrument. Squirt membrane 502 may be thin and present little resistance to the arthroscopic instrument when the instrument is inserted through or removed from passage 508 of hybrid cannula 300. Squirt membrane 502 may be flexible so that the movement of instruments within passage 508 of hybrid cannula 300 is not restricted. Additionally, slots 506 may be created through squirt membrane 502 so that instruments may pass through squirt membrane 502. As depicted in FIG. 9b, squirt membrane 502 may be formed with opening 507 and/or with slots 506. Opening 507 and slots 506 may individually or together combine to have any shape, length, thickness, orientation, and combination thereof, including but not limited to triangle-like slits, a circular hole, a straight slit, an ovular opening, slots and knife slits.

In one embodiment of hybrid cannula 300, body 503a-503b of second portion 500 may be integral with one or more of squirt membrane 502, dam 504, and protrusion 707. Body 503a or 503b may be sufficiently strong to hold membrane 502 or dam 504 and/or to more securely attach second portion 500 to first portion 400. Also, thickness $t_W$ of body 503a or 503b may be thin so that the inner diameter or cannulation of second portion 500 remains as large as possible to allow for a variety of diameters of arthroscopic instruments to pass through hybrid cannula 300.

Dam 504 may prevent fluid from passing through hybrid cannula 300 during, before, and after arthroscopic instruments are passed through hybrid cannula 300. Dam 504 may be preferably thick enough to prevent fluid from leaking but not so thick that it is difficult for the surgeon to pass the arthroscopic instruments through dam 504. Dam 504 may contain openings such as slits 509 to allow instruments to pass through dam 504. These openings flex around an instrument when an instrument is passed through dam 504 and close when dam 504 is in its stable state. These openings in combination with the shape of dam 504 may take the form of any number of shapes, lengths, thicknesses, orientations, and combination thereof, including but not limited to, circular hole(s), ovular opening(s), knife slit(s), tri-slits, duck bill(s), straight slit, quad-slits, overlapping flaps, and small aperture(s). These slits may preferably be long enough to allow instruments to pass though dam 504 without damaging dam 504, even when the instrument has a diameter only slightly smaller than the inner diameter of passage 508 of hybrid cannula 300. Although only one dam 504 is shown in this configuration of second portion 500 of hybrid cannula 300, an embodiment of a hybrid cannula may comprise two or more dams to be located within second portion 500 thereof.

Additionally, the location of dam 504 within the length of hybrid cannula 300 may be anywhere within passage 508 of second portion 500 but may preferably be distal to squirt membrane 502. In one embodiment, dam 504 may be located near the middle of hybrid cannula 300 between proximal end 310b and distal end 320b of second portion 500. The dam location may determine the length of the moment arm acting on the hybrid cannula during instrument insertion and removal. It may be preferable that dam 504 be located in hybrid cannula 300 such that dam 504 can be positioned at or below the level of the skin, no matter how deep hybrid cannula 300 is inserted. However, if dam 504 is too close to distal end 320 of hybrid cannula 300, when articulating instruments are opened, significant leaking or squirting may occur.

The following steps outline a general method for manufacturing hybrid cannula 300, although variations to this method may exist. Embodiments disclosed herein may be manufactured using different processes to produce hybrid cannula 300 having a substantially rigid first portion 400 and substantially flexible second portion 500 with passage 508 which may include dam 504, squirt membrane 502, and other features included therein.

Hybrid cannula 300 may be manufactured by overmolding second portion 500 onto first portion 400, so that no additional assembly is needed. The process of overmolding allows for a cannula with a substantially rigid body composed of one material and a dam composed of another material to be manufactured without the need to secondarily assemble the dam to the body of the cannula.

Figure 10:
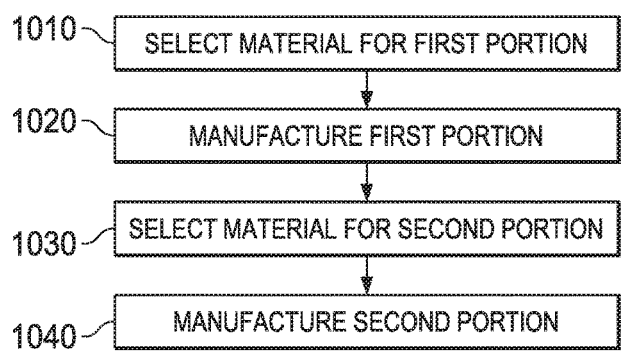
FIG. 10 depicts a flow diagram of one example method of manufacturing a hybrid cannula.

FIG. 10 depicts a flow diagram illustrating one example method for manufacturing a hybrid cannula. In step 1010, a material may be selected for first portion 400 of hybrid cannula 300. As mentioned above, first portion 400 may be manufactured from materials selected for a desired rigidity, with selected features such as threads 404, flange 402, and the like on the outer surface, and may include steps, tapers, surface roughness or other features on the inner surface for contact with second portion 500. The selection of one or more materials for first portion 400 may depend on one or more of an intended length of hybrid cannula 300, a desired inner diameter of hybrid cannula 300, a surgical procedure in which hybrid cannula 300 is to be used, an expected fluid pressure, and the like. Material selection may also factor in weight or density of a material, radioluminescence, color, and transparency.

In step 1020, first portion 400 is manufactured, such as by injection molding or other processes for shaping plastic, metals, ceramic materials or other biocompatible materials known and applicable to biomedical components. In some embodiments, first portion 400 is manufactured through liquid injection molding of a rigid plastic using any number of core pins and mold cavities. For example, material may be injected into a mold and cooled or cured to produce first portion 400 having selected features. After first portion 400 has been molded, the core pins are removed. Steps 1010 and 1020 may be repeated as necessary until all features are formed in first portion 400. First portion 400 may undergo secondary processes such as machining or texturing as preparation for joining with second portion 500.

In step 1030, a material may be selected for second portion 500. Second portion 500 may be manufactured from one or more materials selected for a desired flexibility, smoothness, surface friction, elasticity and the like and for contact with first portion 400.

In step 1040, first portion 400 may be positioned in a second mold. New core pins may be placed into first portion 400 so that an open space remains between first portion 400 and the core pins, except at the points where second portion 500 is meant to begin and end against first portion 400, in order to create the desired features which may include squirt membrane 502 and/or dam 504 features. As an example, in one embodiment, the selected material can be liquid injection molded into empty space in first portion 400 through the process of overmolding. Steps 1030 and 1040 may be repeated as necessary until all features are formed in second portion 500. The material forming second portion 500 adheres to first portion 400, and the core pins are removed from the device leaving second portion 500 permanently fixed to first portion 400. Secondary operations on hybrid cannula 300 may include, but are not limited to, slitting dam 504 located in second portion 500. Further machining or manufacturing processes may be used to customize hybrid cannula 300 for a particular use or patient.

Other embodiments of hybrid cannula 300 may provide additional features, including features relating to a distal end. Example features that may be included in embodiments of hybrid cannula 300 will now be described.

Figure 11:
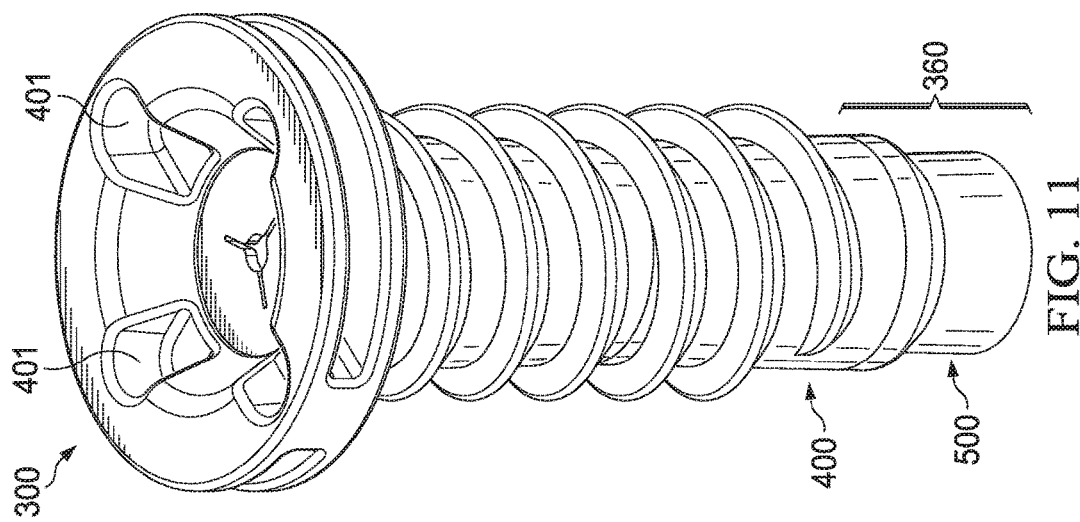
FIG. 11 depicts an isometric view of one embodiment of a hybrid cannula.

FIG. 11 depicts an embodiment of hybrid cannula 300, which comprises similar features as discussed above, and further includes portion 360 of second portion 500 extending beyond the distal tip of first portion 400. Portion 360 may be flexible, semi-rigid, transparent, or have some other characteristic different than the distal tip of first portion 400. In some embodiments, hybrid cannula 300 having portion 360 may allow first portion 400 to be reduced in length, which may be advantageous during insertion, surgery, or removal.

Figure 12:
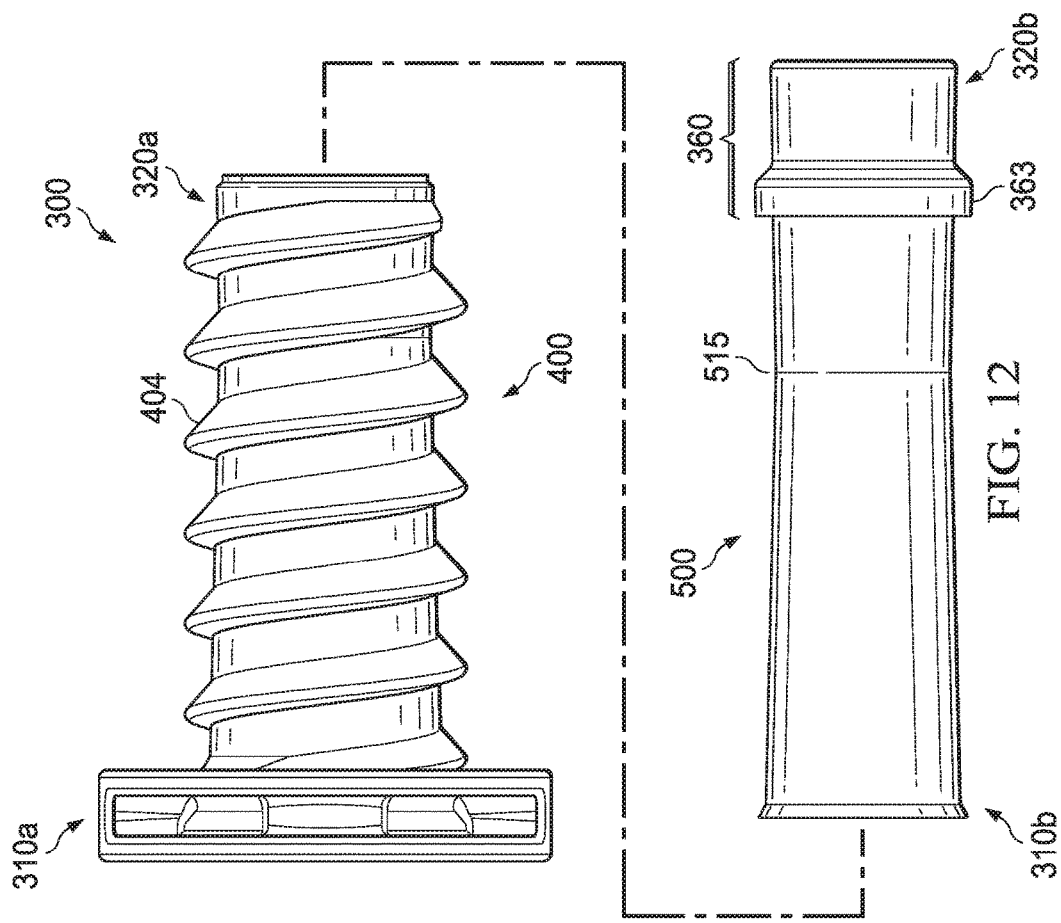
FIG. 12 depicts an exploded view depicting portions of one embodiment of a hybrid cannula.

FIG. 12 depicts an embodiment of hybrid cannula 300 as seen in FIG. 11, in which second portion 500 may include portion 360 having transition section 363. Transition section 363 may provide additional adhesion between second portion 500 and first portion 400, as well as provide a seal off feature which may be necessary for the overmolding process. In one embodiment, dam 504 may be located at seam 515 of second portion 500. The distance between seam 515 and transition section 363 or distal end 320*b* may be shorter than the distance between, for example, dam 504 and proximal end 310*b* (see FIG. 7*b*).

Figure 13A:
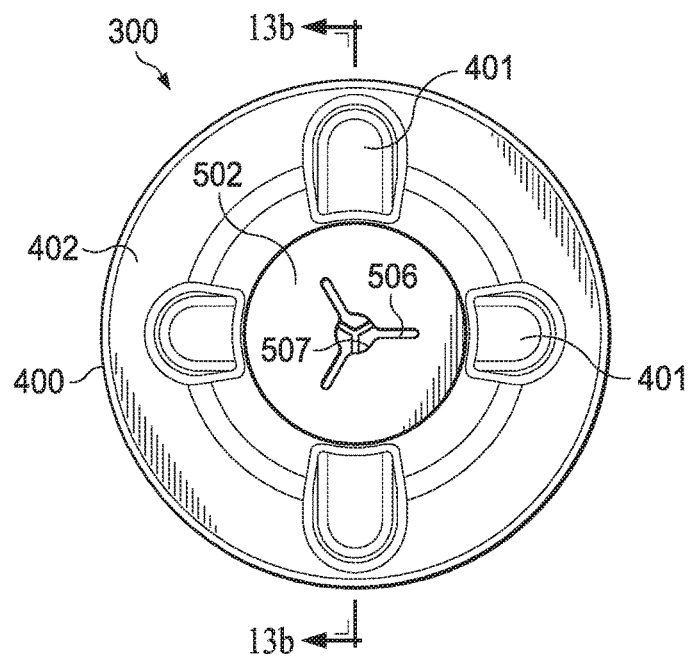
FIGS. 13a and 13b depict a top view and a cross-sectional view of one embodiment of a hybrid cannula.
Figure 13B:
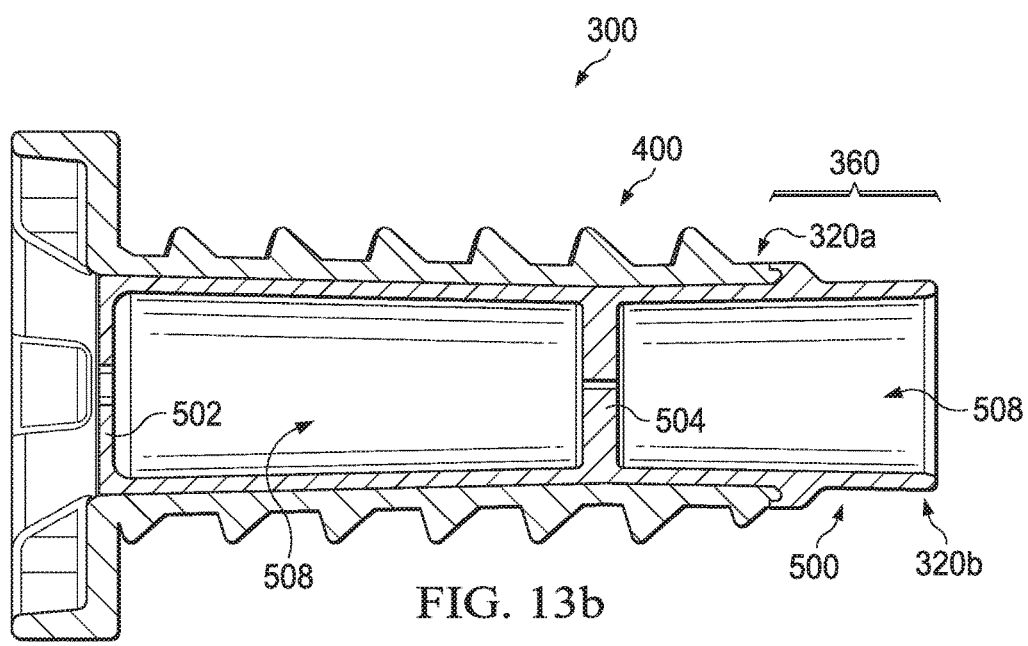

FIGS. 13*a* and 13*b* depict a top view and a cross-sectional view of an embodiment of hybrid cannula 300 as seen in FIGS. 11 and 12 in which distal end 320*b* of second portion 500 has been extended past distal end 320*a* of first portion 400. It may be preferable for end portion 360 to be manufactured from a flexible material described previously. This may allow the surgeon to open articulating instruments while part of the functional tip of the articulating instrument is located within hybrid cannula 300. End portion 360 may stretch and expand while the instrument is articulating. It may be preferable for end portion 360 to be flexible enough for the material to easily stretch during instrument articulation but strong enough to prevent tearing of the material. The range of flexibility is dependent upon the material. Likewise, the distance that end portion 360 at distal end 320*b* of second portion 500 extends past distal end 320*a* of first portion 400 may vary from implementation to implementation.

Figure 14:
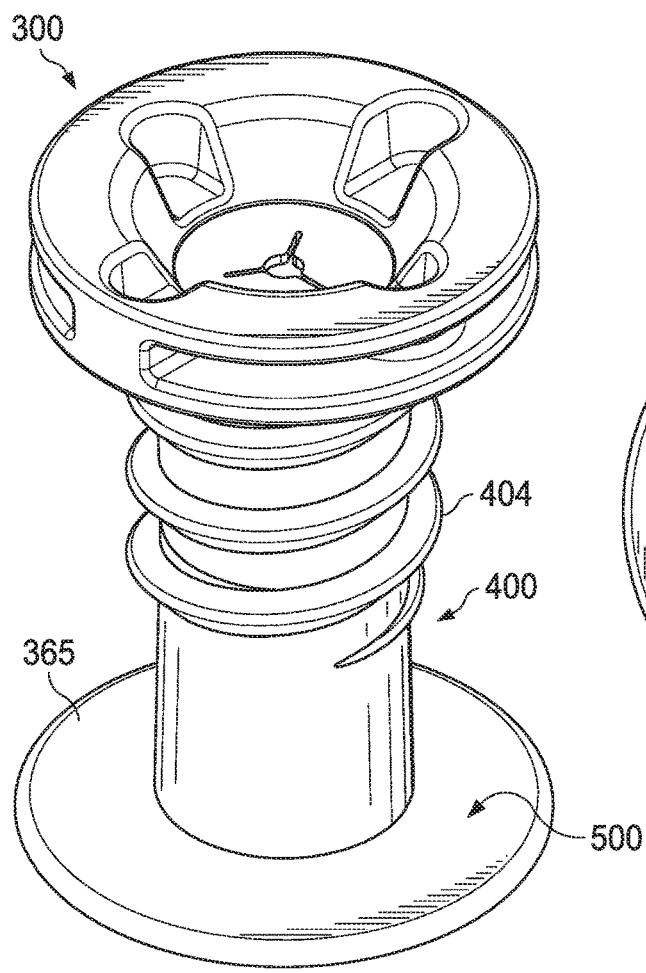
FIG. 14 depicts an isometric view of one embodiment of a hybrid cannula.

FIG. 14 depicts an isometric view of an embodiment of hybrid cannula 300 having flange 365 formed at the distal end of second portion 500 (see FIG. 15*b*) and thread 404 extending only partially along the length of first portion 400.

Figure 15A:
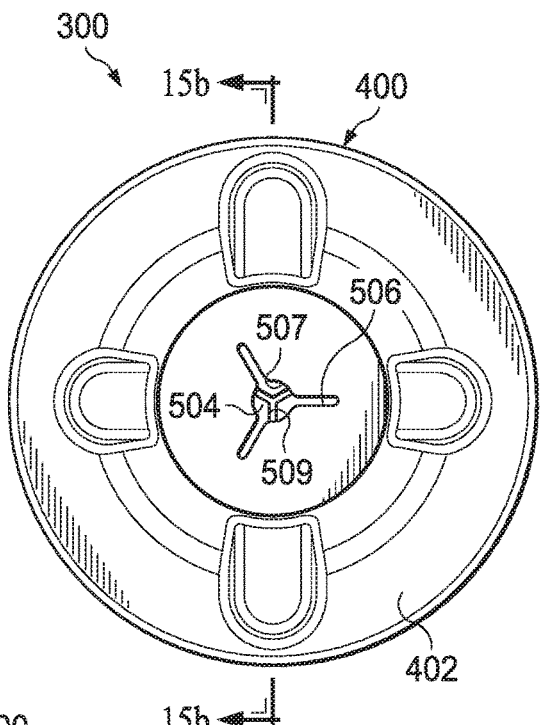
FIGS. 15a and 15b depict a top view and a cross-sectional view of one embodiment of a hybrid cannula.
Figure 15B:
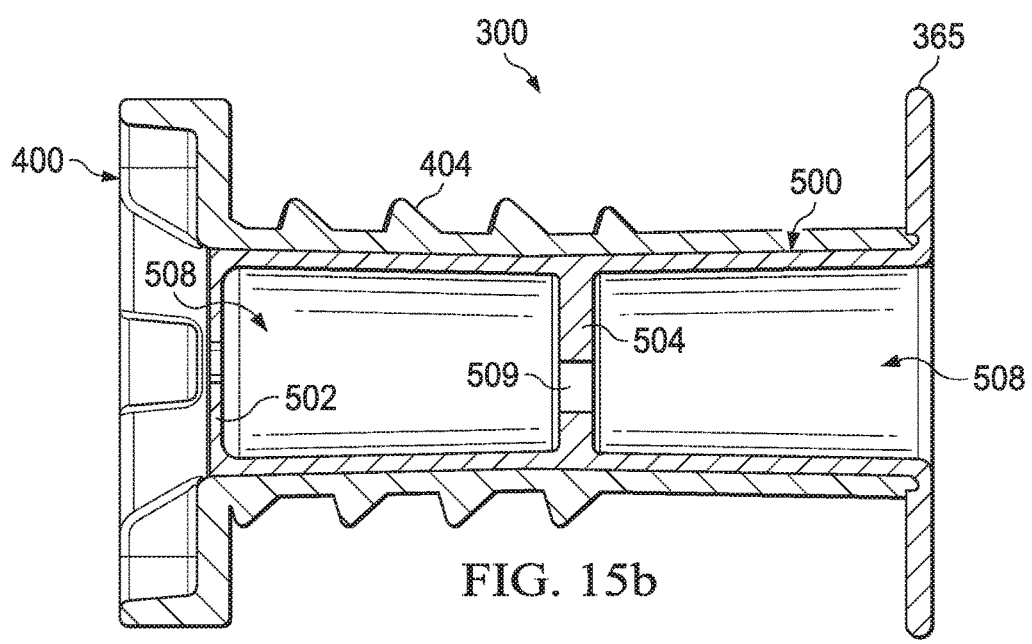

FIGS. 15*a* and 15*b* depict a top view and a cross-sectional view of an embodiment of hybrid cannula 300 as seen in FIG. 14 in which second portion 500 includes flange 365 extending past first portion 400. It may be preferable that second portion flange 365 be manufactured from a flexible material described previously. Flange 365 may ensure that hybrid cannula 300 remains flush to the inner surface of the soft tissue. Flange 365 may have the benefit of staying out of the surgical space as well as potentially improving the field of vision in the surgical space. Flange 365 may have any diameter or shape including but not limited to circular, triangular, and fan shapes and may be beveled or otherwise shaped to allow ease of insertion or removal from a patient. Flange 365 may be thin enough to fold up along the sides of first portion 400 when hybrid cannula 300 is inserted through a portal. Flange 365 may be strong enough not to tear and to hold its original shape once hybrid cannula 300 has been inserted. Additionally, flange 365 may include slits or gaps (not shown) to aid flange 365 in folding up along the sides of first portion 400 when hybrid cannula 300 is inserted through a portal.

On first portion 400 of hybrid cannula 300 thread 404 may terminate near to or away from the distal end of first portion 400. Additionally, second portion 500 of hybrid cannula 300 may extend past external threads 404. External threads 404 may hold hybrid cannula 300 in the soft tissue while the distal end of first portion 400 of hybrid cannula 300 may allow a smooth surface for flange 365 to rest against during insertion of hybrid cannula 300 through the portal. This may prevent excessive protruding of flange 365 against first portion 400 of hybrid cannula 300 during insertion of the device through the portal.

FIGS. 16a and 16b depict side views of one embodiment of hybrid cannula 300 and an obturator 90 (also referred to as a trochar or dilator) useful for inserting hybrid cannula 300 into a patient. As seen in FIG. 16a, obturator 90 may have a central shaft 91 having a length such that end 92 extends beyond a distal end of hybrid cannula 300, and end 92 may be pointed or otherwise shaped for ease of insertion through the soft tissue. Features 93 on obturator 90 may engage hybrid cannula 300 such that by rotating obturator 90 about a central or longitudinal axis, threads 404 of hybrid cannula 300 may engage the soft tissue and advance hybrid cannula 300 into position. Obturator 90 may also be used to remove hybrid cannula 300 or adjust positioning or orientation of hybrid cannula 300 during use. Other insertion methods may be utilized. For example, a long thin metal rod (referred to as a switching stick) is placed through an incision in the skin. The hybrid cannula is placed over the cannulated obturator (the obturator has a hole along its axis). The assembled hybrid cannula and obturator are placed over the switching stick and the hybrid cannula is threaded, pushed or otherwise advanced into the soft tissue. The switching stick is removed and the obturator is removed, leaving the hybrid cannula behind.

Figure 17A:
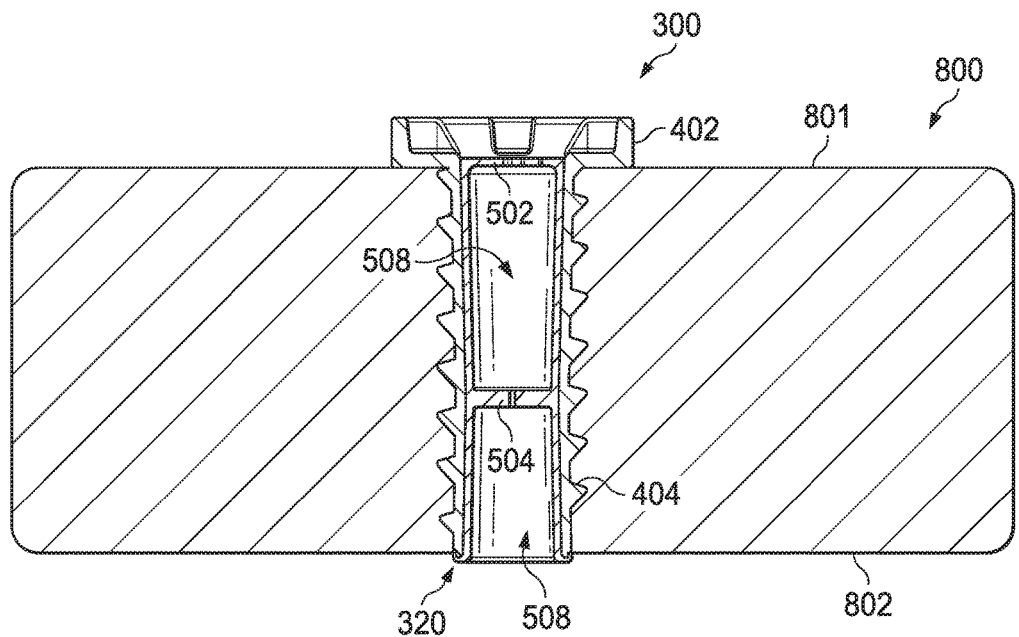
FIG. 17a depicts a cross-sectional view of one embodiment of a hybrid cannula inserted through thick soft tissue.
Figure 17B:
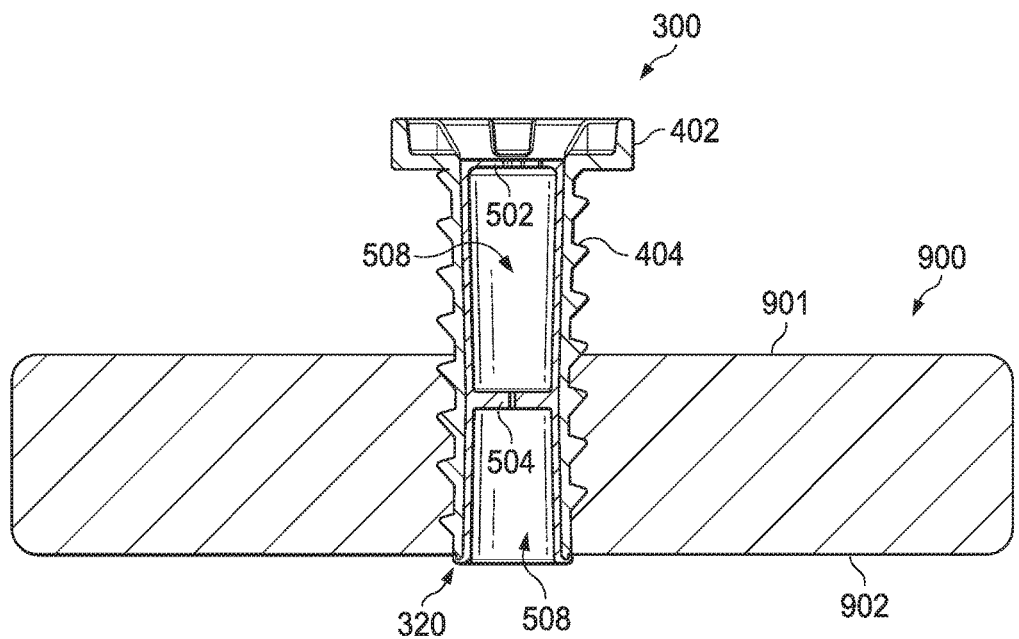
FIG. 17b depicts a cross-sectional view of one embodiment of a hybrid cannula inserted through thin soft tissue.

Attention is now turned to FIGS. 17a-17b which may exemplify the final position of hybrid cannula 300 after inserting it through the soft tissue. Other after-insertion positions of hybrid cannula 300 may also be possible and anticipated. FIG. 17a depicts soft tissue 800 having outer surface 801 and inner surface 802. FIG. 17b depicts soft tissue 900 with outer surface 901 and inner surface 902. It can be seen that soft tissue 800 in FIG. 17a is thicker than soft tissue 900 in FIG. 17b. In both cases, hybrid cannula 300 is shown inserted through the portal made in soft tissues 800 and 900 and, in both cases, dam 504 is located below outer surface 801 or 901 of the soft tissue. This may decrease the moment arm of hybrid cannula 300 and may further prevent the hybrid cannula from falling over, thereby solving a problem common in cannula 100. The moment arm generally refers to the distance from the center of the soft tissue to the point at which an instrument places force on hybrid cannula 300. The location of dam 504 may determine or at least influence the location of the force causing the moment arm.

In one embodiment of hybrid cannula 300, such as depicted in FIG. 17a, proximal flange 402 of hybrid cannula 300 may fit flush against outer surface 801 of soft tissue 800 while distal end 320 of hybrid cannula 300 just extends past inner surface 802 of soft tissue 800. In this case, hybrid cannula 300 is just long enough to be used. If soft tissue 800 is thicker, a longer hybrid cannula 300 may need to be used.

In one embodiment of hybrid cannula 300, such as depicted in FIG. 17b, proximal flange 402 of hybrid cannula 300 abuts or is proximal to outer surface 901 of soft tissue 900 while distal end 320 of hybrid cannula 300 just extends past inner surface 902 of soft tissue 900. In this case, hybrid cannula 300 fits the soft tissue since external threads 404 are engaging soft tissue 900, distal end 320 of hybrid cannula 300 extends just past inner surface 902 of soft tissue 900, and dam 504 of hybrid cannula 300 remains subcutaneous, subdermal, intramuscular, or otherwise beneath outer surface 901 of soft tissue 900. If soft tissue 900 is thinner, a shorter hybrid cannula 300 may need to be used in order for the dam to remain subcutaneous, subdermal, intramuscular, or otherwise beneath outer surface 901 of soft tissue 900.

One method for using hybrid cannula 300 may involve preparing the surgical site. For example, an x-ray, MRI, or other imaging system may be used to determine the thickness of soft tissue 900 and other tissue near the desired surgery site. Depending upon the thickness of soft tissue, hybrid cannula 300 may be selected or prepared accordingly for insertion. In some embodiments, a kit may include different lengths, inner diameters of a passage, dam positions, dam thicknesses, squirt membrane thicknesses, etc. of hybrid cannula 300.

Selection of a desired hybrid cannula 300 may be based on a feature of hybrid cannula 300. For example, a hybrid cannula 300 may be selected to ensure that a dam is positioned at some point in the tissue, such as approximately half way, close to the surface, close to the surgical site, or some point in between.

As mentioned above, embodiments disclosed herein may be manufactured such that a variety of hybrid cannula 300 options exist with dam 504 positioned in various locations within passage 508 of second portion 500. In some embodiments, hybrid cannula 300 may be cut or otherwise modified in the operating room for a desired surgery.

Advancement of hybrid cannula 300 into a patient may involve translation or rotation or some combination thereof. For example, hybrid cannula 300 may be pushed or threaded into soft tissue. In some embodiments, an arthroscope or other visualization tool may be advanced into the patient to see how far hybrid cannula 300 needs to be advanced. In some embodiments, markings on hybrid cannula 300 may enable advancement of hybrid cannula 300 to a desired depth. Example markings may include, but are not limited to, tool markings, laser lines, threads on the exterior of first portion 400 of hybrid cannula 300, etc. In one embodiment, an arthroscope or other visualization tool may be used to determine whether hybrid cannula 300 has been inserted properly through the soft tissue.

In some embodiments, hybrid cannula 300 may be advanced until the distal end contacts a selected body part, opening, space, or tissue. For example, in some embodiments in which hybrid cannula 300 has a flexible distal end, the tip may be advanced until the tip contacts the desired tissue, which may allow a surgeon to operate without debris approaching the surgical site as the surgeon is operating.

Once advanced to a desired depth, one or more tools may be advanced into the patient via a passage in the hybrid cannula.

Removal of hybrid cannula 300 may include removal of tools from inside passage 508, rotating or pulling hybrid cannula 300 to disengage threads 404 from tissue, and removing hybrid cannula 300 from the patient. One or more sutures may be applied to close the incision.

Figure 18A:
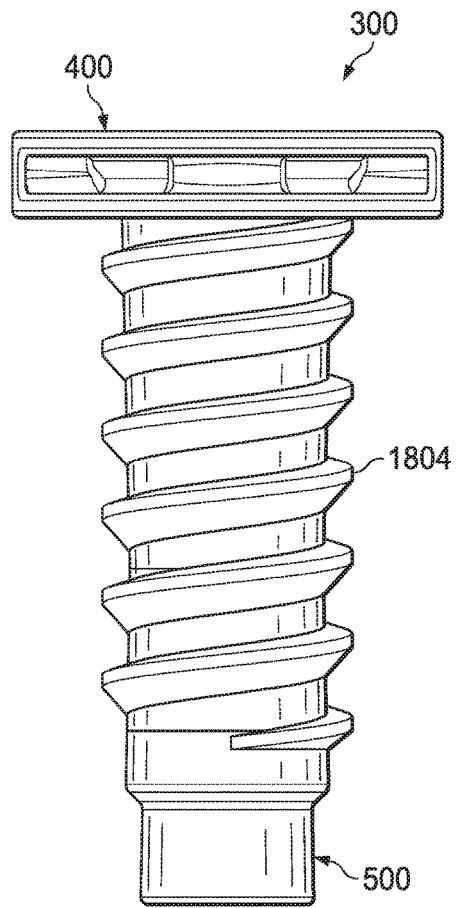
FIGS. 18a and 18b depict side and cross-sectional views of one embodiment of a hybrid cannula.
Figure 18B:
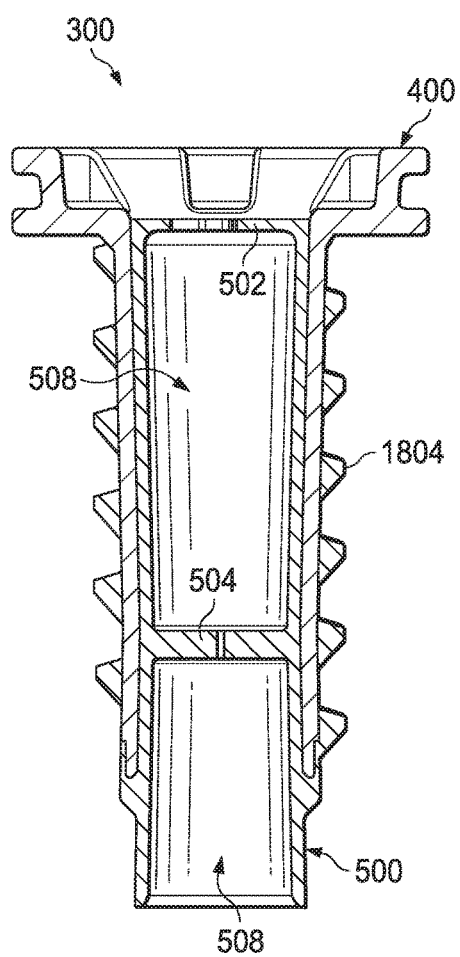
Figure 19A:
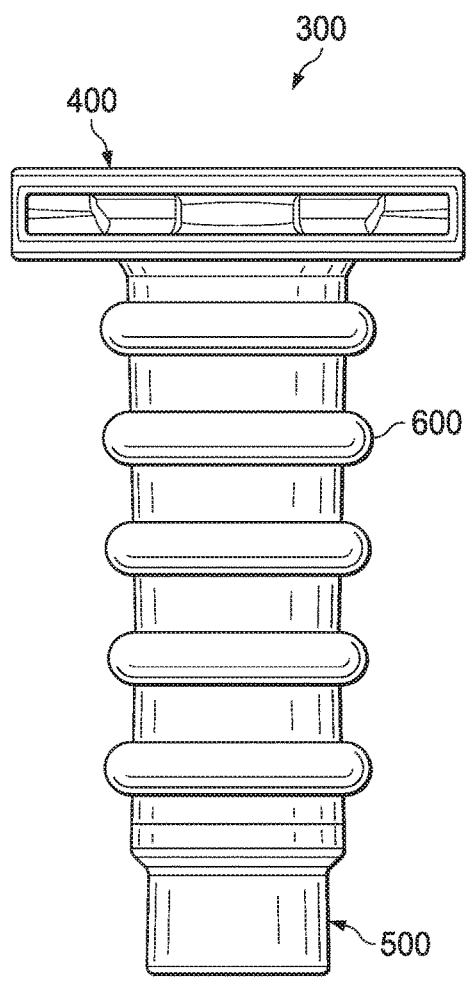
FIGS. 19a and 19b depict side and cross-sectional views of one embodiment of a hybrid cannula.
Figure 19B:
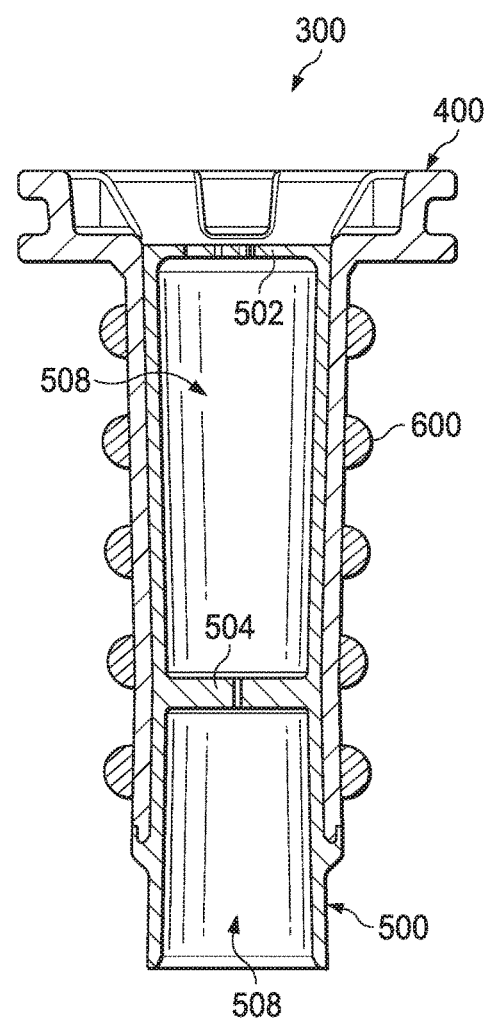
Figure 20A:
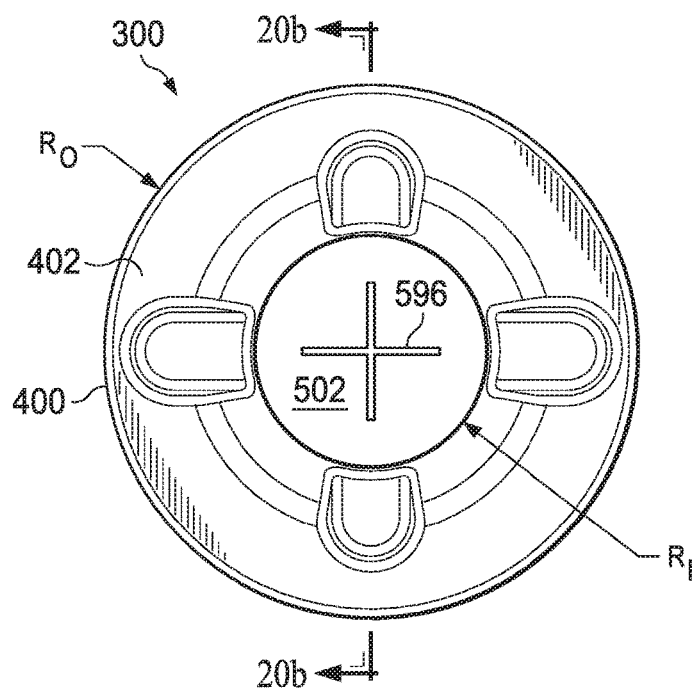
FIGS. 20a-20e depict top, cross-sectional, isometric and exploded views of one embodiment of a hybrid cannula.
Figure 20B:
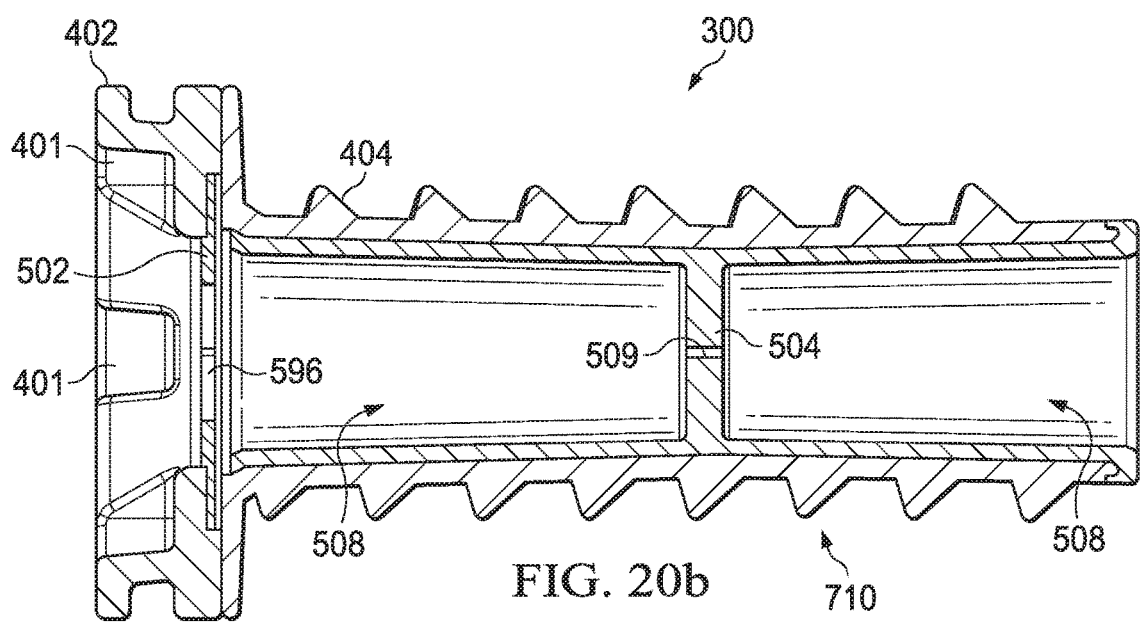
Figure 20C:
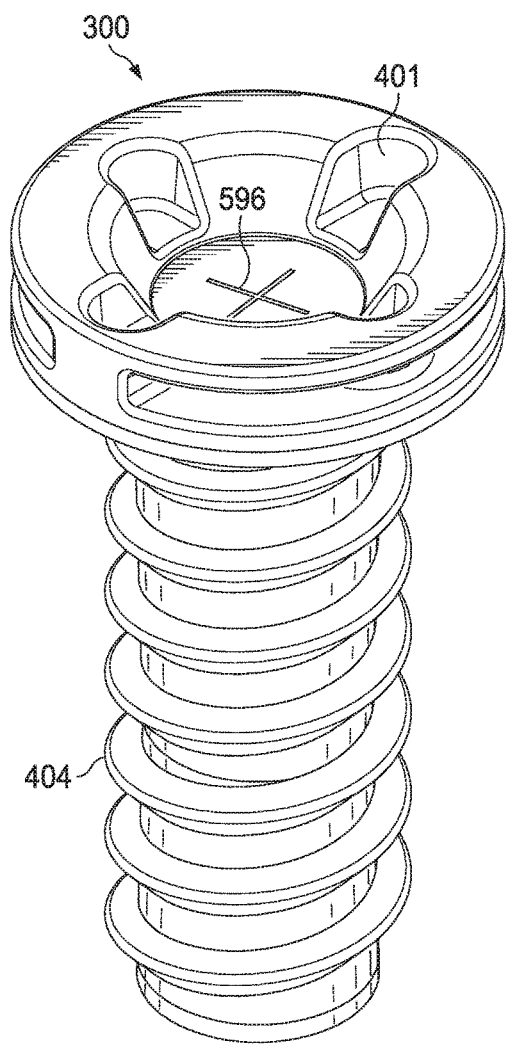
Figure 20D:
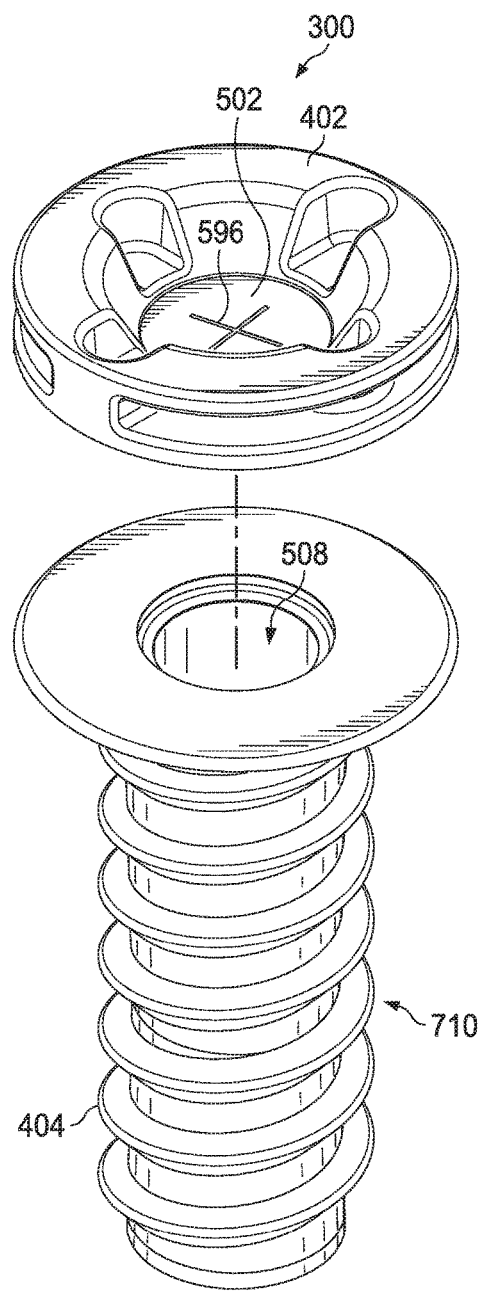
Figure 20E:
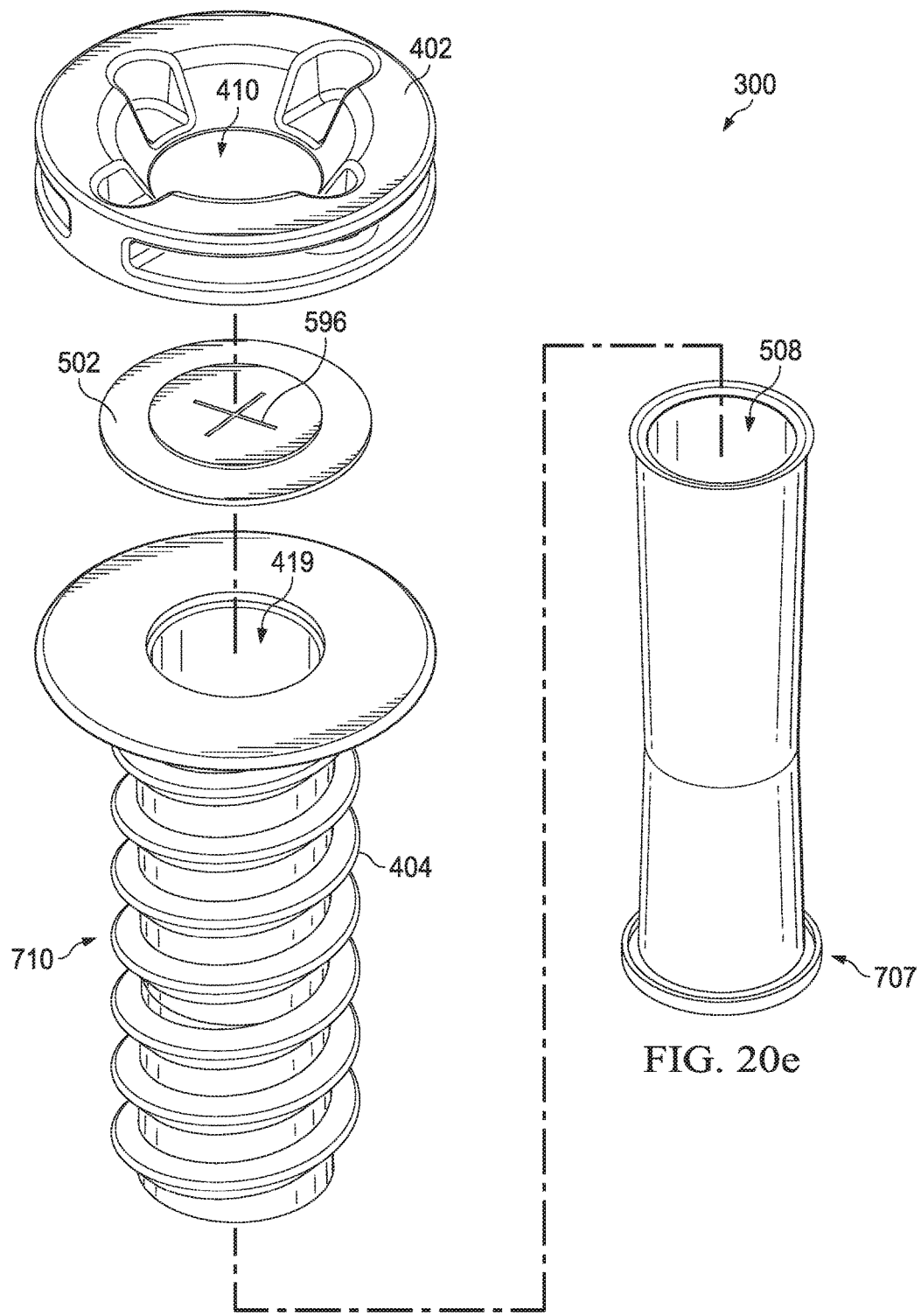

FIGS. 18a-18b and FIGS. 19a-19b depict embodiments of hybrid cannula 300 which may be manufactured using multiple overmolding passes or manufactured to have selected features. As depicted in FIGS. 18a and 18b, first portion 400 may be formed in a first process and second portion 500 may be overmolded or otherwise formed in a second process to form internal features such as dam 504 as well as external features such as thread 1804. As depicted in FIGS. 19a and 19b, more than one overmolding process may be used to manufacture features onto hybrid cannula 300. For example, first portion 400 may be formed in a first process. A first overmolding process may be used to form dam 504 and other internal features of second portion 500, and a second overmolding process may be used to manufacture thread or ribbing 600. Other features or molding processes may be useful.

FIGS. 20a-20e depict embodiments of cannula 300 manufactured using multiple molding processes. For example, manufacturing cannula 300 may include forming flange 402 and overmolding a first flexible material to form thin membrane 502, forming body 710 and overmolding a second flexible material to form dam 504, and joining flange 402 with body 710 to form hybrid cannula 300 such that passage 508 is formed with thin membrane 502 and dam 504 therein. Flange 402 and body 710 may be assembled and fixed together using a number of methods including, but not limited to, for example, adhesives, sonic welding, and/or mechanical fixation. Because hybrid cannula 300 depicted in FIGS. 20a-20e is manufactured in parts (the four portions— flange 402, a first flexible material forming thin membrane 502, body 710, and a second flexible material forming dam 504 with or without protrusion 707 at the distal end), opening 507 and/or slits 506 are not needed (see FIG. 9b). Since a core pin does not pass through thin membrane 502 during molding of second portion 500, opening 507 and/or slits 506 are not necessary. Thus, thin membrane 502 may undergo a secondary slitting operation to manufacture slits 596 without opening 507 for example.

As described above, a hybrid cannula can be manufactured in parts. Each part of the hybrid cannula can be a single piece or a monolithically formed component as illustrated in FIGS. 20a-20e. In some embodiments, a hybrid cannula may be made of a plurality of parts and one or more of the parts may be made of discrete components. Example embodiments of such a hybrid cannula and methods of manufacturing same will now be described.

Figure 21:
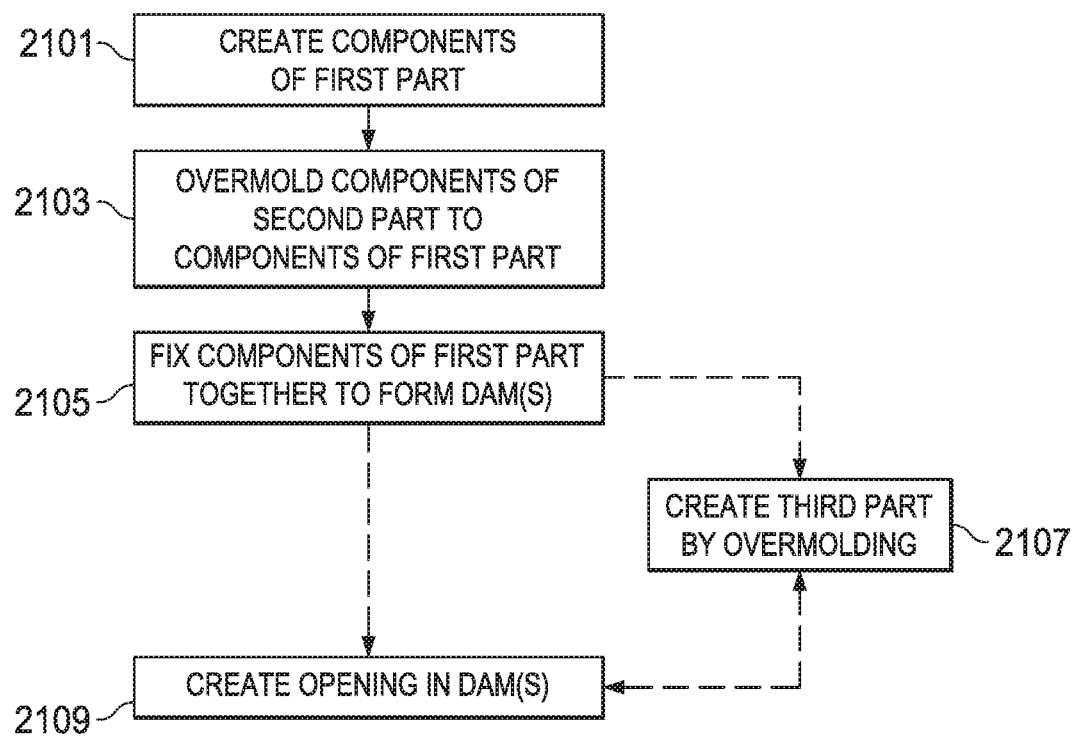
FIG. 21 depicts a flow diagram of one example method of manufacturing a hybrid cannula.

FIG. 21 depicts a flow diagram of one example method of manufacturing a hybrid cannula from parts with discrete components. In some embodiments, the method may comprise creating components of a first part (step 2101). The first part may have at least two discrete components. Each of the discrete components of the first part may have a proximal end, a distal end, and a channel extending between the proximal end and the distal end. The first part may be made of a rigid material. Examples of a suitable rigid material may include, but are not limited to, polycarbonate, polyetheretherketone (PEEK), acrylonitrile butadiene styrene (ABS), polyethylene, titanium, stainless steel, other plastics and metals, etc. The first part may provide the structure of the body of the hybrid cannula.

The method may further comprise creating components of a second part by overmolding (step 2103). The second part may also have at least two discrete components. Each of the discrete components of the second part may be created by overmolding a non-rigid material to the channel in each of the discrete components of the first part. Examples of a suitable non-rigid material may include, but are not limited to, an elastic substance such as thermoplastic elastomer, polyurethane, silicone, rubber, etc. The second part may include various types of features including but not limited to thick dams, thin dams, squirt membranes, and duck bill dams inside the hybrid cannula.

The discrete components of the first part may then be fixed together to create a unit (also referred to as an integrated piece) with a cylindrical body (step 2105). In some embodiments, this unit or integrated piece may resemble a tube. As described above, each of the discrete components of the second part is overmolded to the channel of each of the discrete components of the first part. Fixing the discrete components of the first part together may therefore include fixing the discrete components of the second part together such that the discrete components of the second part form one or more dams inside the tube. The discrete components can be fixed together in various ways, including but not limited to gluing, bonding, welding, interlocking, and/or mechanical fitting.

Optionally, in some embodiments, the method may proceed to create an opening in the dam(s) formed by the second part inside the tube (step 2109). The opening may be created by slitting the dam(s) with an instrument such as a knife. Such an opening in each dam may have any number, shape, orientation, and length of slits. The slits may allow passage of an instrument while the dam(s) may prevent air or fluid from passing through the hybrid cannula. The dam may also be molded with multiple openings, including but not limited to slots or holes, in any number, shape, or variation which may or may not require creating an opening in the dam as described in this step 2109. Step 2109 may not be necessary in the case that an opening such as a slit, slot, or hole is naturally present in the dam, after the components of the first part are fixed together, and is sufficient for the purposes of the dam. Accordingly, each dam of a hybrid cannula manufactured according to the method described above may comprise an opening, manufactured and/or naturally formed, for allowing passage of an instrument and a partition for preventing air or fluid from passing through the hybrid cannula.

In some embodiments, a hybrid cannula may be manufactured with only the first part and the second part. In such embodiments, the first part may have external threads, rings, or protrusions. In some embodiments, the second part may be overmolded to at least a portion of the inner surface of the first part. Alternatively, the second part may provide features such as external threads, rings, and/or protrusions and/or an extension, a flange, or a combination thereof at a distal tip. More specifically, in some embodiments, the second part may be overmolded up to the entire length of the first part, inside and/or outside of the first part. For example, the second part may be overmolded to all of the inner surface of the first part and provide internal features such as dam(s). Additionally, the second part may be overmolded around the first part so that the second part contains internal features as well as external features.

Optionally, in some embodiments, the method may further comprise creating a third part by overmolding the unit, for instance, which may resemble a tube, with a non-rigid material (step 2107). As illustrated in FIG. 21, step 2107 may be performed before or after step 2109. In some embodiments, the second part and the third part may be made of the same non-rigid material. The third part may provide an extension, a flange, or a combination thereof at a distal end of the hybrid cannula. The third part may have a smooth surface or it may have external threads, rings, or protrusions. Again, in some embodiments, the third part is not required for the hybrid cannula to function.

Figure 22:
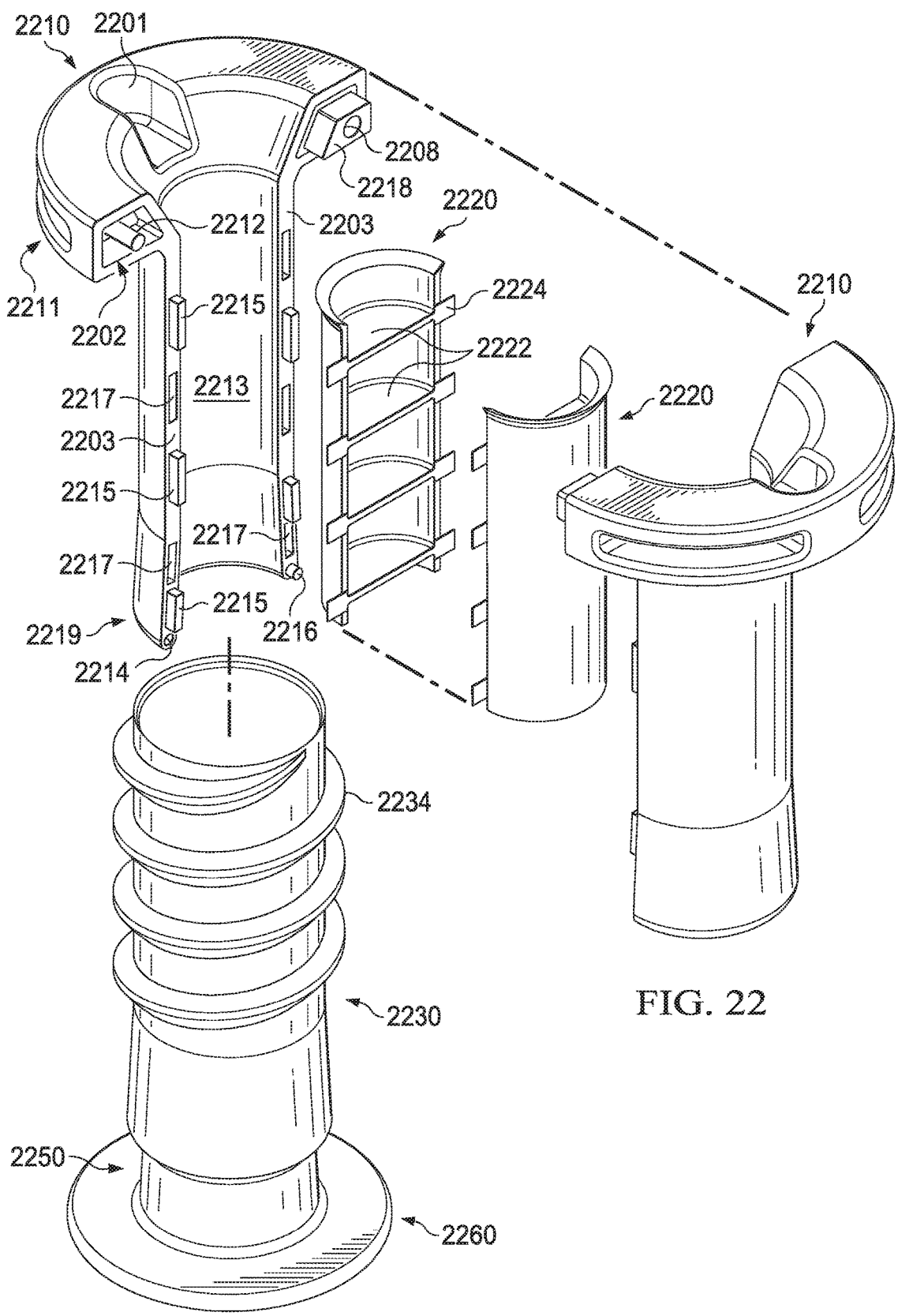
FIG. 22 depicts an exploded view showing distinct parts and their discrete components of one embodiment of a hybrid cannula.
Figure 23A:
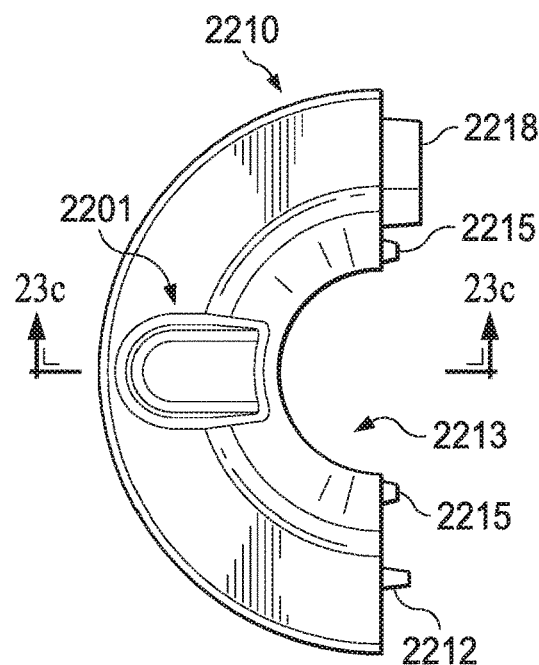
FIGS. 23a and 23b depict top views of discrete components of a first part according to one embodiment of a hybrid cannula.
Figure 23B:
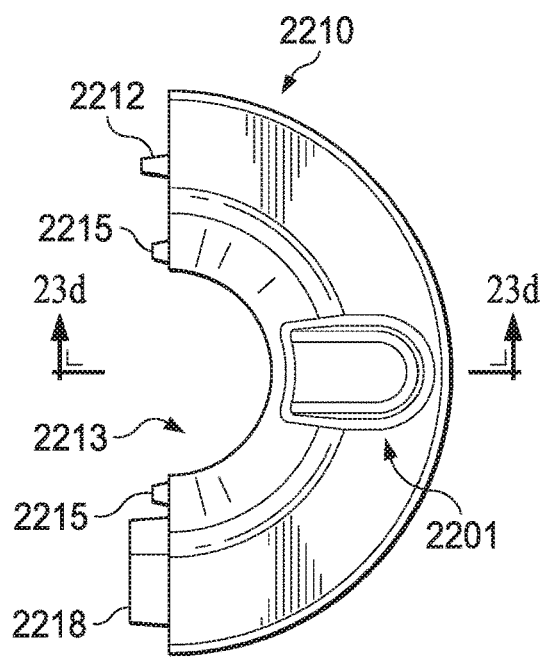
Figure 23E:
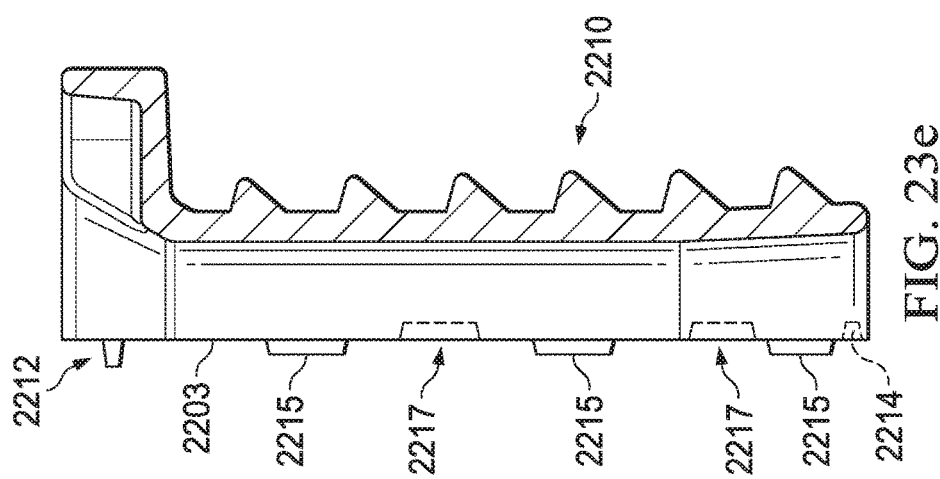
FIGS. 23c and 23d depict cross-sectional views of the components shown in FIGS. 23a and 23b along line 23c and 23d and FIG. 23e shows another embodiment of FIG. 23d.
Figure 23D:
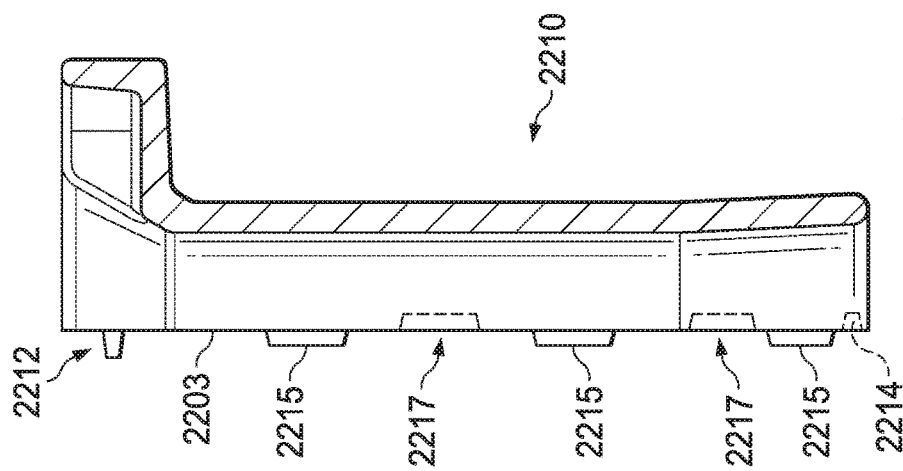
Figure 23C:
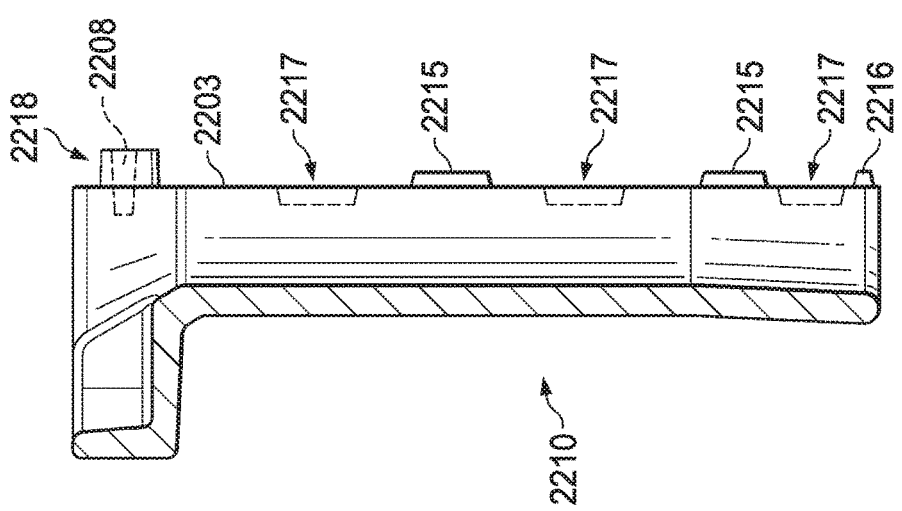

FIG. 22 depicts an exploded view showing an example of first part 2210, second part 2220, and optional third part 2230. One embodiment of first part 2210 is further illustrated in FIGS. 23a-b which depict top views of discrete components of first part 2210 and FIGS. 23c-d which depict cross-sectional views of the components shown in FIGS. 23a and 23b along lines 23c and 23d. FIG. 23e shows another embodiment of FIG. 23d. Some embodiments of second part 2220 are further illustrated in FIGS. 24a and 24b which respectively depicts a front view of a component of second part 2220. Some embodiments of third part 2230 are further illustrated in FIGS. 25a and 25b which respectively depicts a cross-sectional view of third part 2230. Note the example cross-sections shown in FIGS. 23c-d are taken alone lines 23c and 23d at an angle (e.g., 90 degree) from surfaces of the components to be assembled/coupled (e.g., edges 2203 of the components of first part 2210). When the components of first part 2210 shown in FIGS. 23c-d are assembled/coupled, edges 2203 would naturally form a seam in the middle of the cross-sections. Those skilled in the art will appreciate that this type of artifact is part of the manufacturing process and may be visible on embodiments of a hybrid cannula disclosed herein (see e.g., hybrid cannula 2610 shown in FIG. 26e and hybrid cannula 3100 shown in FIG. 31). For the sake of clarity, this type of manufacturing artifact is not depicted in the cross-sectional views of the drawings so as not to interfere with the depiction of other features.

As illustrated in FIG. 22 and FIGS. 23a-d, a pair of discrete components of first part 2210 can be seen as two halves identical to one another (e.g., two identical components shown in FIG. 23e). Such identical components of the first part can be made from the same mold or identical molds. Each of the discrete components of the first part may have a proximal end, a distal end, and channel 2213 extending between the proximal end and the distal end. Each of the discrete components can be monolithically formed and may include various features such as head portion 2211, pin 2212, stud 2218, protruding interlocking features 2215, recessed interlocking features 2217, and distal tip 2219. Head portion 2211 may include a tool portion, such as tool portion 2201 depicted here, configured to receive an instrument. Head portion 2211 may also include pin hole 2208 configured to receive a pin on the head portion of another first part component. In this example, head portion 2211 may further include recessed area 2202 configured to receive a stud or projection on the head portion of another first part component. Additionally, each of the discrete components of first part 2210 may have protruding interlocking features 2215 and recessed interlocking features 2217 juxtaposed along edges 2203 of channel 2213. Furthermore, distal tip 2219 may have pin hole 2214 and pin 2216 located on opposite sides of channel 2213 as shown in FIG. 22. Pin 2216 and pin hole 2214 can be used for alignment, making sure that the two components of first part 2210 line up correctly. As illustrated in FIGS. 23a-d, these features are configured to complement one another such that the two components of first part 2210 can be mechanically coupled together to form a unit, for instance, one that resembles a tube, and in some embodiments this can occur even before second part 2220 is overmolded to first part 2210.

In FIGS. 22 and 23a-d, first part 2210 is shown to have a smooth external surface. In some embodiments, with or without a third part, the first part can have various external features, including but not limited to external threads, rings, or protrusions (see e.g., FIG. 23e). These external features can help while inserting the hybrid cannula into a surgical area and/or keeping fluid from flowing around the hybrid cannula during surgery between the soft tissue and the external surface of the hybrid cannula. These external features may be of any size or shape and may start and end at any point on the external surface of first part 2210.

Figure 24A:
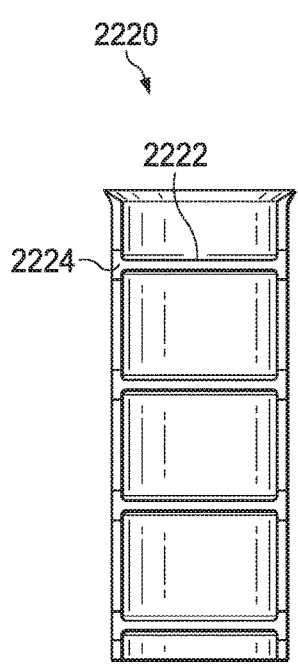
FIGS. 24a and 24b respectively depicts a front view of a component of a second part according to one embodiments of a hybrid cannula.
Figure 24B:
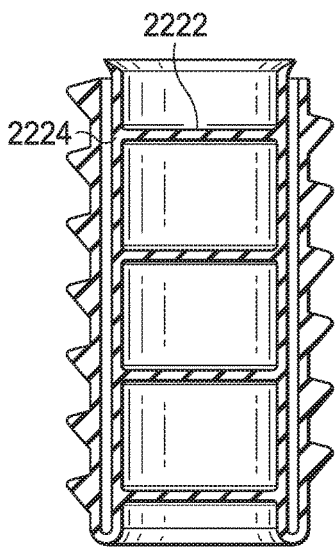
Figure 25A:
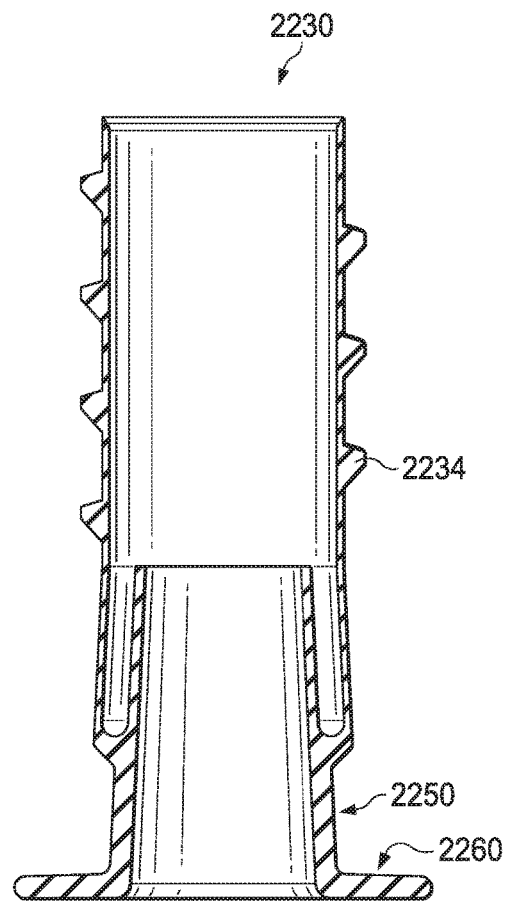
FIGS. 25a and 25b respectively depicts a cross-sectional view of a third part according to one embodiments of a hybrid cannula.
Figure 25B:
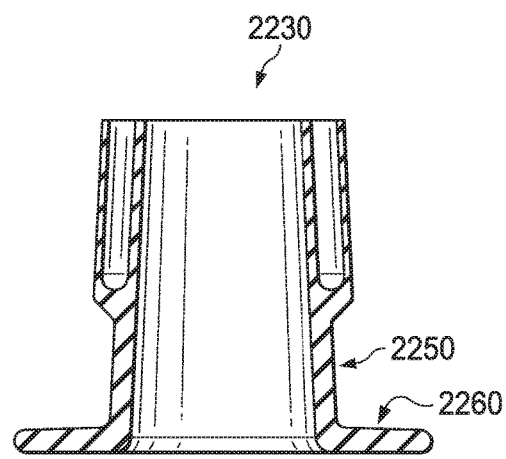
Figure 26C:
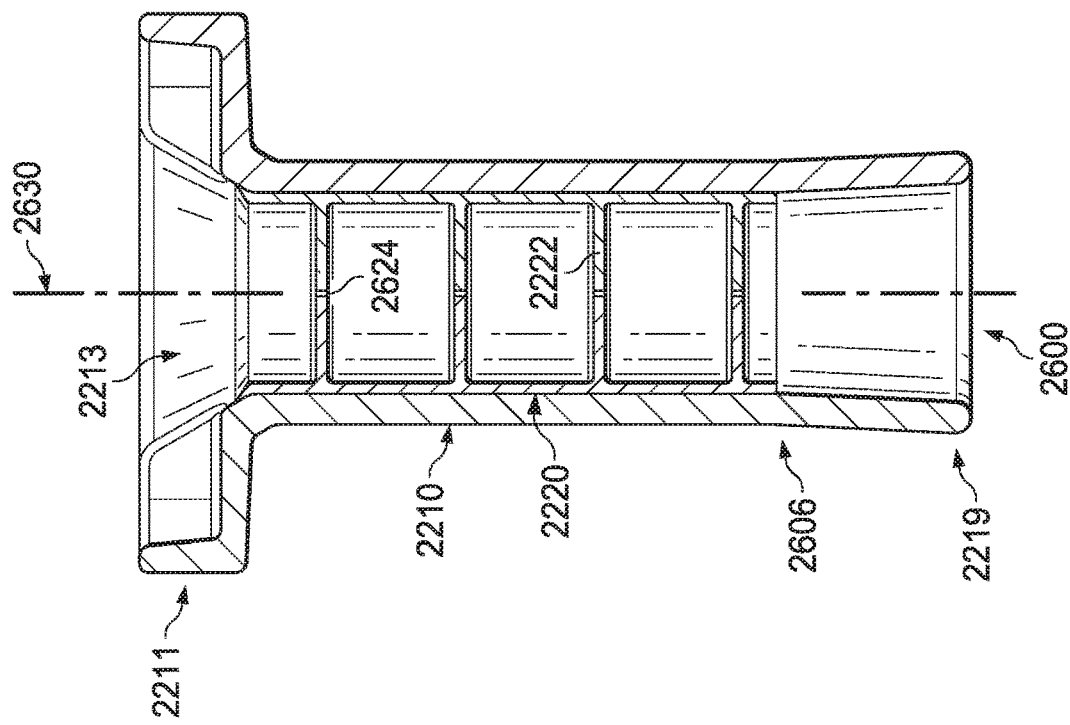
FIGS. 26a-d illustrate by example one embodiment of a process of manufacturing a hybrid cannula.
Figure 26B:
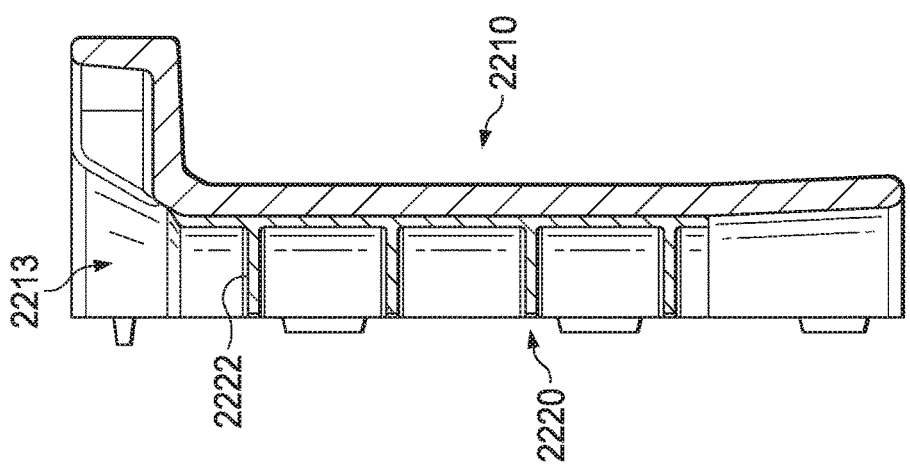
Figure 26A:
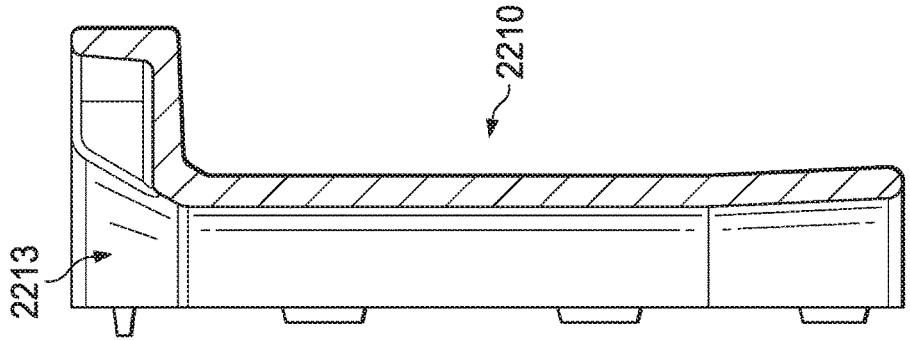

Referring to FIGS. 22, 24a-b, and 26a-b, second part 2220 may be overmolded to first part 2210 to create at least one dam 2222 in channel 2213 of first part 2210. In some embodiments, tabs 2224 of second part 2220 may be overmolded to edges 2203 along channel 2213 of first part 2210, between protruding interlocking features 2215 and recessed interlocking features 2217. As exemplified by FIGS. 22 and 24a-b, tabs 2224 may be configured in various ways. For instance, tabs 2224 may be configured to extend beyond the edges of second part 2220 (FIG. 22) or along the edges of second part 2220 (FIGS. 24a-b). In some embodiments, tabs 2224 may not be necessary. Likewise, second part 2220 can have various configurations. In some embodiments, the second part can be overmolded to an entire length of the first part. As illustrated in FIG. 26b, in some embodiments, second part 2220 can be overmolded to a portion along channel 2213 of first part 2210 to form dam(s) 2222 in channel 2213. Like first part 2210 in FIG. 22, a pair of discrete components of second part 2220 can be identical to one another, as shown in FIG. 26c. The identical components of the second part can be made from the same mold or identical molds.

As described above, first part 2210 may be of a rigid material and second part 2220 may be of a non-rigid material. By overmolding a non-rigid material to a rigid material and by making parts of a hybrid cannula in discrete components, more than two dams can be formed inside the hybrid cannula. This is not possible in other overmolded cannulas because the core of a monolithically formed rigid part is exposed axially instead of normally to its axis. Embodiments disclosed herein can provide access to components of the first part in the mold which is normal to the first part's axis, making it possible to form more than two dams inside a hybrid cannula. In some embodiments, the second part may be overmolded to the first part to create three or more dams 2222 in a channel of a first part. Although four dams 2222 are shown in FIG. 26b, those skilled in the art will appreciate that other implementations with a different number of dams may be possible.

In some cases, having multiple dams inside a hybrid cannula can provide advantages. For example, a sharp instrument passing through a conventional cannula with an internal dam may cut through or puncture the flaps of the dam, instead of passing through the opening/slits of the dam. One way to address this issue is to make the dam substantially thin such that the dam is not easily punctured when a force is applied (for instance, by the passage of an instrument) and the instrument will slide through the opening. However, a single thin dam may not be sufficient to keep the air or fluid from passing through the cannula. Embodiments of a hybrid cannula can solve this problem by forming multiple thin dams inside the hybrid cannula to hold back the air/fluid pressure, while allowing the instrument to pass through the opening/slits.

The overmolded components of the first part can then be fixed together as described above to create a unit such as hybrid cannula 2600 shown in FIG. 26c. In some embodiments, a unit thus created may resemble a tube. In some embodiments, hybrid cannula 2600 can be manufactured with only first part 2210 and second part 2220 overmolded to first part 2210 to form dam(s) 2222. Opening 2624 in dam(s) 2222 may be created by slitting dam(s) 2222 with an instrument such as a knife along central axis 2630 of hybrid cannula 2600. Opening 2624 may be configured in various ways and have any number, shape, orientation, and length of slits or it may be a "natural slit" and left as is in post processing.

As illustrated in FIG. 26c, hybrid cannula 2600 may have elongated cylindrical body 2606 extending between the proximal end and the distal end of hybrid cannula 2600, with head portion 2211 located at the proximal end. In this example, second part 2220 does not extend beyond distal tip 2219 of first part 2210 and, as such, hybrid cannula 2600 does not have an extension. In some embodiments, a second part may be overmolded to first part 2210 to extend beyond the distal end of first part 2210 to form an extension, a flange, and/or a combination thereof for the hybrid cannula.

In some embodiments, a third part may optionally be overmolded to a unit, for instance, one that resembles a tube, made of a first part and a second part described above. In some embodiments, such a third part may have a smooth surface (see e.g., FIG. 25b). In some embodiments, a third part may have external features such as external threads, rings, or protrusions. These external features may be of any shape and size and may start and end at any point along the external surface of the hybrid cannula. In the example shown in FIG. 22, with second part 2220 overmolded to first part 2210 and the two components of the first part fixed together to form dam(s) 2222 in channel 2213 as described above, third part 2230 is overmolded to first part 2210 to create threads 2234, extension 2250, and flange 2260 (also shown in FIG. 25a). As further illustrated in FIG. 26d, in addition to threads 2634, third part 2230 may be overmolded to first part 2210 to create distal tip 2670 (with extension 2650 and flange 2660) for hybrid cannula 2610. FIG. 26e depicts a perspective view of hybrid cannula 2610 manufactured via the example process described above and illustrated in FIGS. 26a-d. In some embodiments, the third part may include external features in addition to or instead of the threads. Such external features may be configured to facilitate insertion of the hybrid cannula into a surgical area and/or keep the fluid from passing around the hybrid cannula during surgery between the external surface of the hybrid cannula and the soft tissue.

Figure 27:
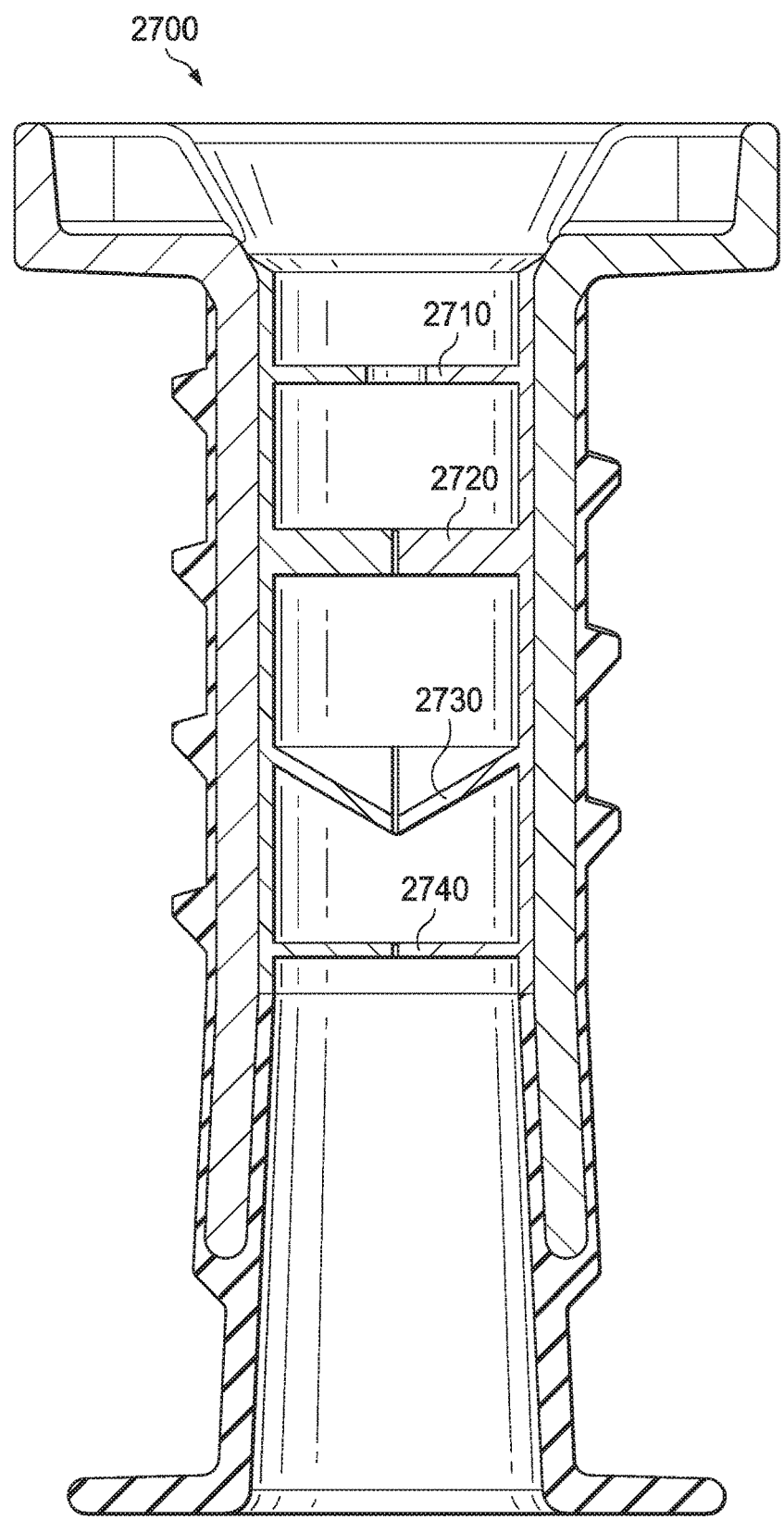
FIG. 27 depicts a cross-sectional view of a hybrid cannula with various types of features, including external and internal overmolded features.

The dams formed as described above can have various configurations. FIG. 27 depicts a cross-sectional view of hybrid cannula 2700 with various types of features, including external overmolded features described above and internal overmolded squirt membrane 2710, thick dam 2720, thin duck bill dam 2730, and thin dam 2740. One skilled in the art would recognize that the internal features shown in FIG. 27 are only a few of the many possibilities of types of dams/membranes that may be formed in the hybrid cannula. In some embodiments, a hybrid cannula may have multiple dams of the same or different configurations. As described above, each such dam may comprise an opening and a partition, the partition dividing a channel in the hybrid cannula into separate spaces.

Figure 26D:
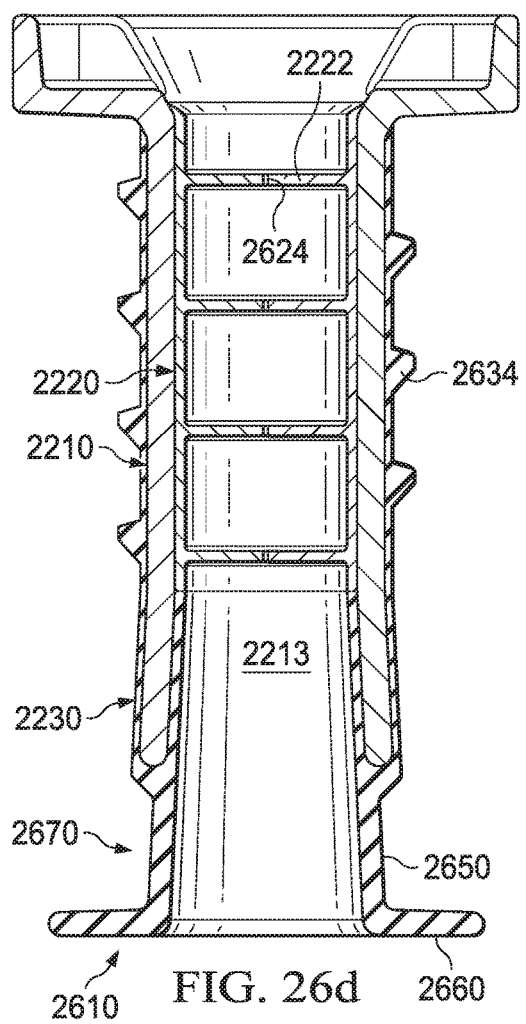
Figure 26E:
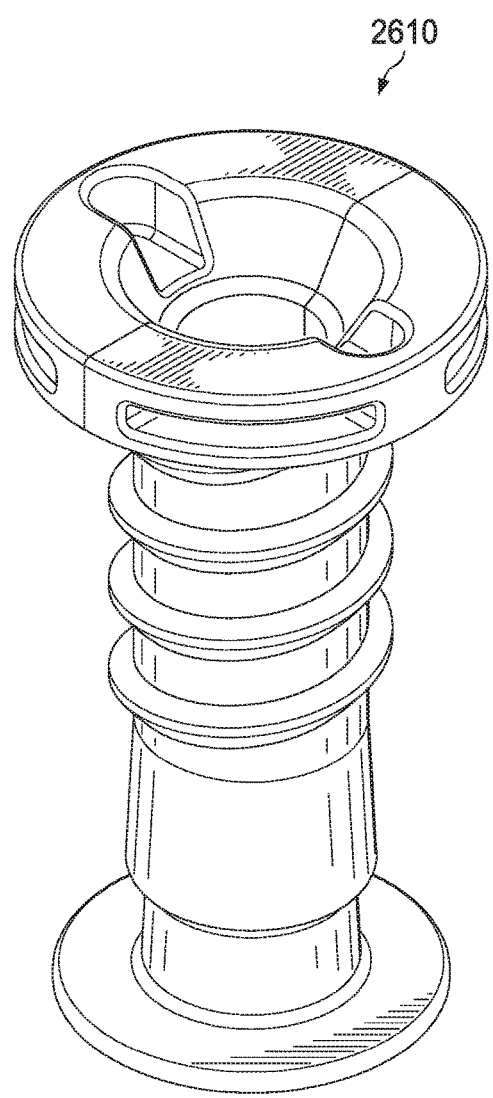
FIG. 26e depicts a perspective view of a hybrid cannula manufactured via the example process illustrated in FIGS. 26a-d.
Figure 30:
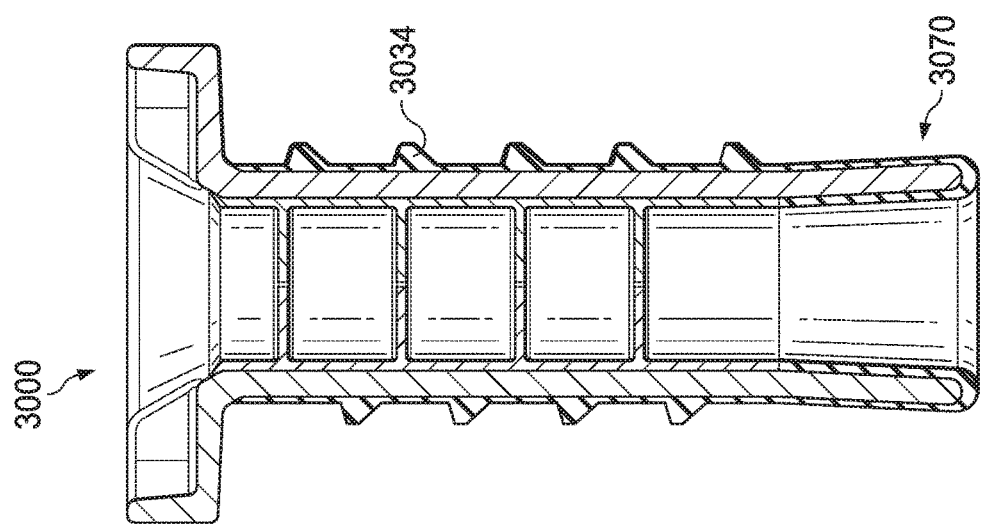
FIG. 30 depicts a cross-sectional view of one embodiment of a hybrid cannula with an overmolded third part providing features such as external threads for the hybrid cannula.
Figure 29:
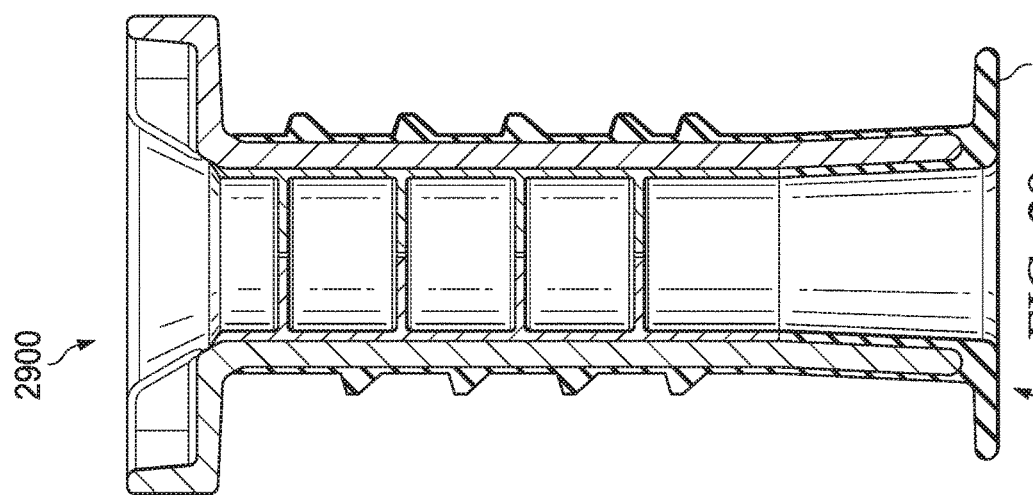
FIG. 29 depicts a cross-sectional view of one embodiment of a hybrid cannula with an overmolded third part providing features such as a flange for the hybrid cannula.
Figure 28:
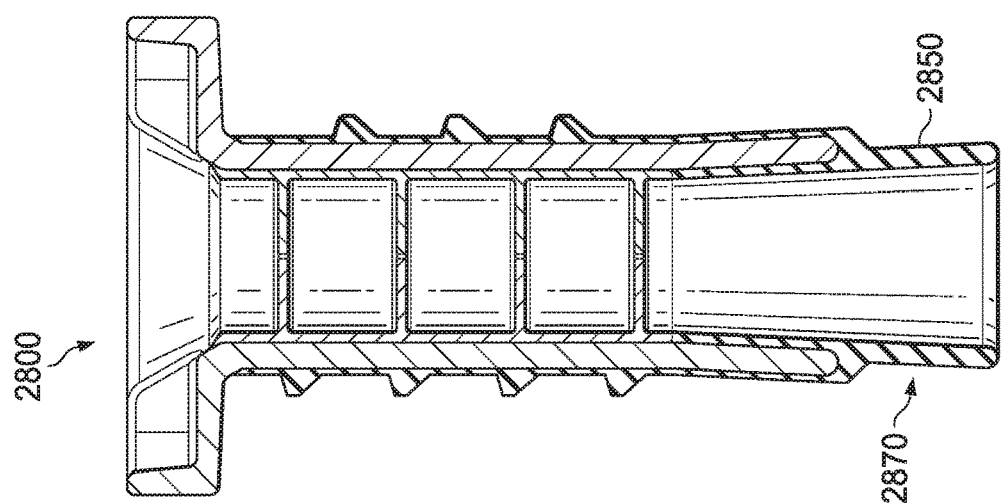
FIG. 28 depicts a cross-sectional view of one embodiment of a hybrid cannula with an overmolded third part providing features such as an extension for the hybrid cannula.

In the example of FIG. 26d, hybrid cannula 2610 comprises extension 2650 and flange 2660 at distal tip 2670. In some embodiments, a hybrid cannula may not have an extension or flange (see, for example, FIGS. 26c and 30). Other implementations may also be possible. For example, FIG. 28 depicts a cross-sectional view of one embodiment of hybrid cannula 2800 with an overmolded third part providing extension 2850 at distal tip 2870 of hybrid cannula 2800. As another example, FIG. 29 depicts a cross-sectional view of one embodiment of hybrid cannula 2900 with an overmolded third part providing flange 2960 without an extension at distal tip 2970 of hybrid cannula 2900. Yet another example is shown in FIG. 30 which depicts a cross-sectional view of one embodiment of hybrid cannula 3000 with an overmolded third part providing overmolded features such as external threads 3034, without an extension or flange at distal tip 3070 of hybrid cannula 3000.

Figure 31:
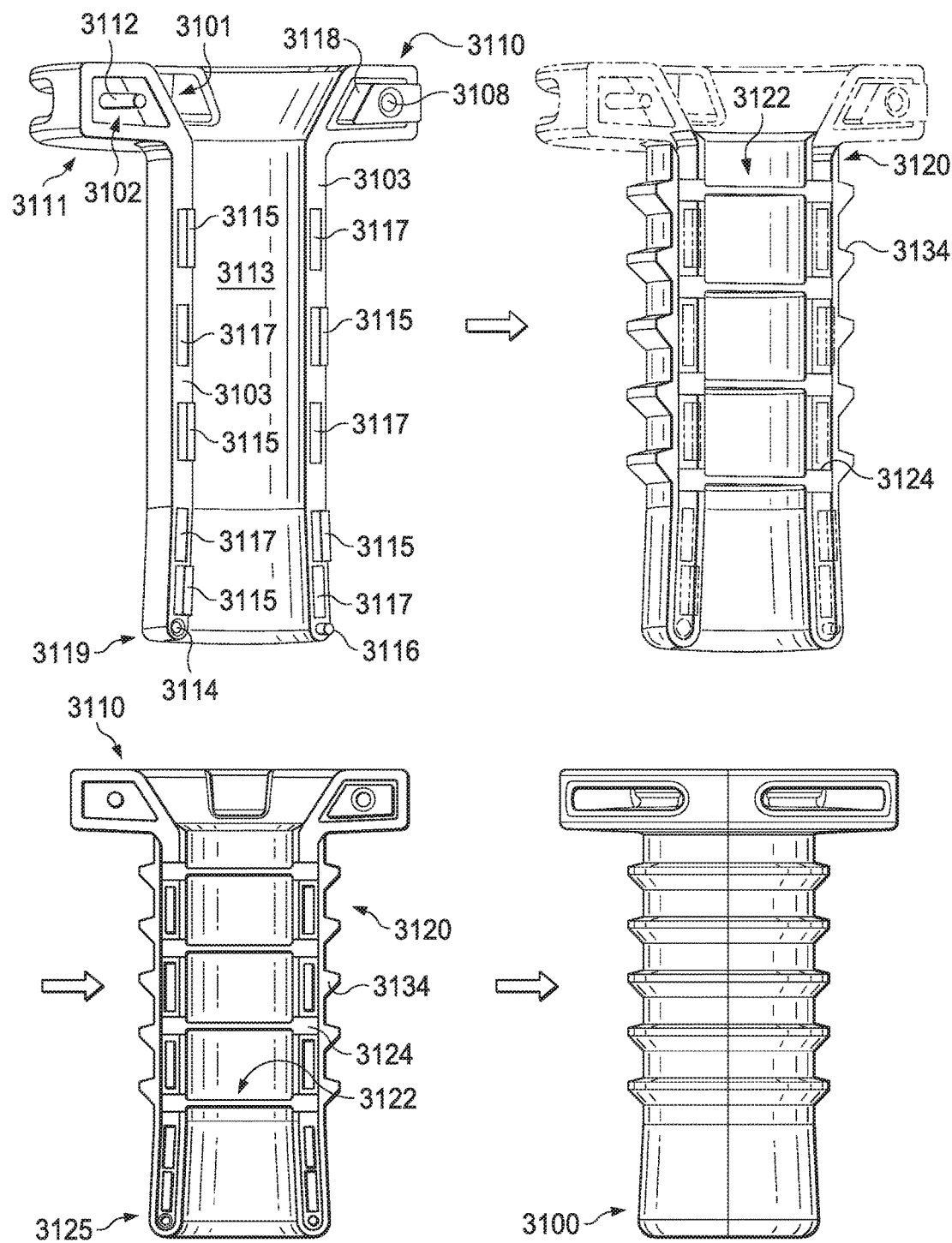
FIG. 31 illustrates by example one embodiment of a process of manufacturing one embodiment of a hybrid cannula with distinct parts and their discrete components.

In some embodiments, a hybrid cannula may be manufactured with two distinct parts and without a third part. FIG. 31 depicts by example one embodiment of a process of manufacturing a hybrid cannula from two distinct parts, each having a set of discrete components. Such components may be made from the same mold or identical molds. Each of the discrete components of first part 3110 may have a proximal end, a distal end, and channel 3113 extending between the proximal end and the distal end. Each of the discrete components can be monolithically formed and may include various features such as head portion 3111, pin 3112, stud 3118, protruding interlocking features 3115, recessed interlocking features 3117, and distal tip 3119. Head portion 3111 may include a tool portion, such as tool portion 3101 depicted here, configured to receive an instrument. Head portion 3111 may also include pin hole 3108 configured to receive a pin on the head portion of another first part component (not shown). In this example, head portion 3111 may further include recessed area 3102 configured to receive a stud or projection on the head portion of another first part component. Additionally, each of the discrete components of first part 3110 may have protruding interlocking features 3115 and recessed interlocking features 3117 juxtaposed along edges 3103 of channel 3113. Furthermore, distal tip 3119 may have pin hole 3114 and pin 3116 located on opposite sides of channel 3113 as shown in FIG. 31.

Each component of first part 3110 may be overmolded with second part 3120 to form various internal features such as dam(s) 3122, tab(s) 3124, and external features such as threads, ribs, rings, or protrusions 3134. These external features may be of any size or shape and may start and end at any point on the external surface of first part 3110. As illustrated in FIG. 31, this process can produce semi-complete part 3125 which can then be aligned and fixed with another semi-complete part to form a complete hybrid cannula (hybrid cannula 3100).

Figure 32:
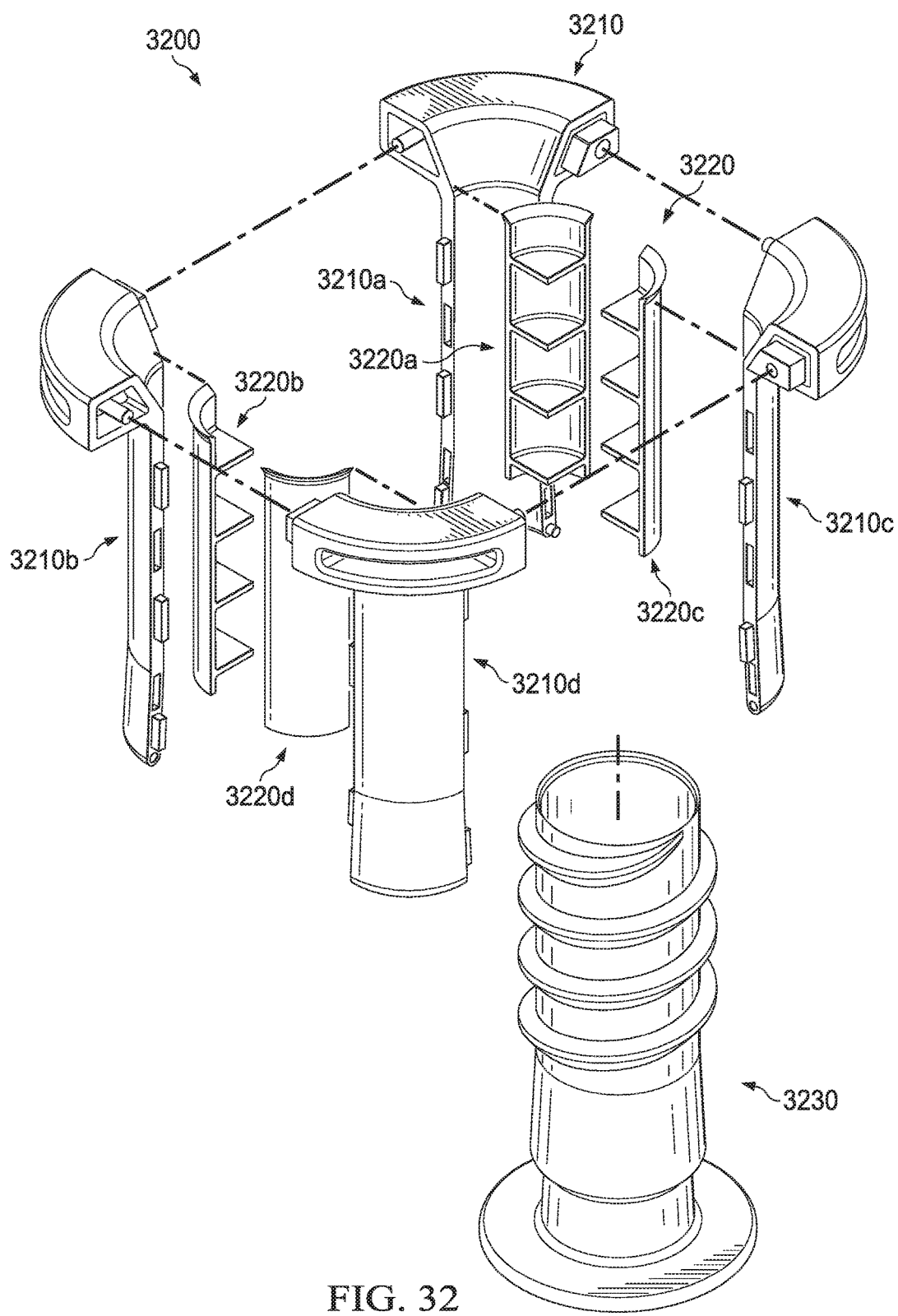
FIG. 32 depicts an exploded view showing one embodiment of a hybrid cannula with distinct parts and their discrete components.

The detailed description and the specific examples described above, while indicating the preferred embodiments, are given by way of illustration only and not by way of limitation. Descriptions of known materials and manufacturing techniques may be omitted so as not to unnecessarily obscure the disclosure in detail. Various substitutions, modifications, additions and/or rearrangements within the spirit and/or scope of the underlying inventive concept will become apparent to those skilled in the art from this disclosure. For example, a person skilled in the art will appreciate that the same manufacturing process described above with reference to FIGS. 21-31 could be performed with any number of components for each part of a hybrid cannula. Therefore, some embodiments of a hybrid cannula may be manufactured with two or more components per part. As a specific example, FIG. 32 depicts one embodiment of hybrid cannula 3200 having first part 3210, second part 3220, and optional third part 3230. First part 3210 has a set of discrete components 3210a, 3210b, 3210c, and 3210d. Correspondingly, second part 3220 has a set of discrete components 3220a, 3220b, 3220c, and 3220d overmolded to components 3210a, 3210b, 3210c, and 3210d of first part 3210. These components may be aligned, coupled, and overmolded with third part 3230 to form hybrid cannula 3200 in a manner similar to the manufacturing processes described above with reference to FIGS. 21-31.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited to only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the accompanying appendices, a term preceded by "a" or "an" (and "the" when antecedent basis is "a" or "an") includes both singular and plural of such term, unless clearly indicated otherwise (i.e., that the reference "a" or "an" clearly indicates only the singular or only the plural). Also, as used in the description herein and in the accompanying appendices, the meaning of "in" includes "in" and "on" unless the context clearly dictates otherwise.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/Figures should be considered only as exemplary, and not limiting, unless otherwise specifically noted.

It should be understood that the inventive concepts disclosed herein are capable of many other modifications. To the extent such modifications fall within the scope of the appended claims and their equivalents, they are intended to be covered by this patent. It should also be understood that the term "a" as used herein generally means "one or more" and is not intended to be construed in a singular sense. In addition, the operations described in connection with the methods of the disclosure need not necessarily be executed in the sequence described, as they may be executed in a different sequence consistent with the principles of the disclosure.

What is claimed is:

1. A product manufactured by a process of manufacturing a cannula, the process comprising:
   creating a first part of a rigid material and having at least two components, each of the at least two components of the first part having a proximal end, a distal end, and a channel extending between the proximal end and the distal end;
   creating a second part of a non-rigid material and having at least two components, each of the at least two components of the second part having at least one dam portion overmolded and permanently fixed to the channel of each of the at least two components of the first part;
   fixing the at least two components of the first part overmolded with the at least two components of the second part together to form the cannula with at least one dam; and
   overmolding a third part of a non-rigid material to at least a portion of the first part, at least a portion of the second part, or both, wherein the third part comprises an extension, a flange, a distal tip or a combination thereof at a distal end of the cannula.

2. The product of claim 1, wherein the at least two components of the first part are identical to each other.

3. The product of claim 1, wherein the at least one dam comprises:
   an opening configured for allowing passage of an instrument; and
   a partition configured for preventing air or fluid from passing through the cannula.

4. The A product manufactured by a process of manufacturing a cannula, the process comprising:
   creating a first part of a rigid material and having at least two components, each of the at least two components of the first part having a proximal end, a distal end, and a channel extending between the proximal end and the distal end;
   creating a second part of a non-rigid material and having at least two components, each of the at least two components of the second part having at least one dam portion overmolded and permanently fixed to the channel of each of the at least two components of the first part;
   fixing the at least two components of the first part overmolded with the at least two components of the second part together to form the cannula with at least one dam; and
   overmolding a third part of a non-rigid material to at least a portion of the first part, at least a portion of the second part, or both, wherein the third part comprises a smooth surface and has no external threads, rings, or protrusions.

5. The product of claim 4, wherein the at least two components of the first part are identical to each other.

6. The product of claim 4, wherein the at least one dam comprises:
   an opening configured for allowing passage of an instrument; and
   a partition configured for preventing air or fluid from passing through the cannula.

7. A product manufactured by a process of manufacturing a cannula, the process comprising:
   creating a first part of a rigid material and having at least two components, each of the at least two components of the first part having a proximal end, a distal end, and a channel extending between the proximal end and the distal end;
   creating a second part of a non-rigid material and having at least two components, each of the at least two components of the second part having at least one dam portion overmolded and permanently fixed to the channel of each of the at least two components of the first part;
   fixing the at least two components of the first part overmolded with the at least two components of the second part together to form the cannula with at least one dam; and
   overmolding a third part of a non-rigid material to at least a portion of the first part, at least a portion of the second part, or both, wherein the third part comprises external threads, rings, protrusions, or a combination thereof, the external threads starting and ending at any point along a length of the cannula.

8. The product of claim 7, wherein the at least two components of the first part are identical to each other.

9. A product manufactured by a process of manufacturing a cannula, the process comprising:

creating a first part of a rigid material and having at least two components, each of the at least two components of the first part having a proximal end, a distal end, and a channel extending between the proximal end and the distal end, wherein the first part comprises external threads, rings, protrusions, or a combination thereof, the external threads starting and ending at any point along a length of the cannula;

creating a second part of a non-rigid material and having at least two components, each of the at least two components of the second part having at least one dam portion overmolded and permanently fixed to the channel of each of the at least two components of the first part; and fixing the at least two components of the first part overmolded with the at least two components of the second part together to form the cannula with at least one dam.

10. The product of claim 9, wherein the at least two components of the first part are identical to each other.

11. A product manufactured by a process of manufacturing a cannula, the process comprising:

creating a first part of a rigid material and having at least two components, each of the at least two components of the first part having a proximal end, a distal end, and a channel extending between the proximal end and the distal end;

creating a second part of a non-rigid material and having at least two components, each of the at least two components of the second part having at least one dam portion overmolded and permanently fixed to the channel of each of the at least two components of the first part, wherein the second part is overmolded to at least a portion and up to an entire length of the first part; and fixing the at least two components of the first part overmolded with the at least two components of the second part together to form the cannula with at least one dam.

12. The product of claim 11, wherein the at least two components of the first part are identical to each other.

13. A product manufactured by a process of manufacturing a cannula, the process comprising:

creating a first part of a rigid material and having at least two components, each of the at least two components of the first part having a proximal end, a distal end, and a channel extending between the proximal end and the distal end;

creating a second part of a non-rigid material and having at least two components, each of the at least two components of the second part having at least one dam portion overmolded and permanently fixed to the channel of each of the at least two components of the first part, wherein the second part comprises external threads, rings, protrusions, a distal tip, a flange, an extension, or a combination thereof, the external threads starting and ending at any point along a length of the cannula; and fixing the at least two components of the first part overmolded with the at least two components of the second part together to form the cannula with at least one dam.

14. The product of claim 13, wherein the at least two components of the first part are identical to each other.

15. A product manufactured by a process of manufacturing a cannula, the process comprising:

creating a first part of a rigid material and having at least two components, each of the at least two components of the first part having a proximal end, a distal end, and a channel extending between the proximal end and the distal end;

creating a second part of a non-rigid material and having at least two components, each of the at least two components of the second part having at least one dam portion overmolded and permanently fixed to the channel of each of the at least two components of the first part; and fixing the at least two components of the first part overmolded with the at least two components of the second part together to form the cannula with at least one dam.

16. The product of claim 15, wherein the rigid material comprises a polycarbonate, polyetheretherketone (PEEK), acrylonitrile butadiene styrene (ABS), polyethylene, titanium, stainless steel, plastic, or metal.

17. The product of claim 15, wherein the non-rigid material comprises a thermoplastic elastomer, polyurethane, silicone, or rubber.

18. The product of claim 15, wherein the at least two components of the first part are identical to each other.

19. The product of claim 15, wherein the at least two components of the first part are fixed together by gluing, bonding, welding, interlocking, or mechanical fitting.

20. The product of claim 15, wherein the at least one dam comprises:

an opening configured for allowing passage of an instrument; and a partition configured for preventing air or fluid from passing through the cannula.

* * * * *